(12) United States Patent
Bendory et al.

(10) Patent No.: US 11,202,557 B2
(45) Date of Patent: Dec. 21, 2021

(54) EAR VISUALIZATION AND TREATMENT SYSTEM

(71) Applicant: 3NT MEDICAL LTD., Rosh Ha'ayin (IL)

(72) Inventors: Ehud Bendory, Herzliya (IL); Eran Bendory, Maccabin-Re'ut (IL)

(73) Assignee: 3NT Medical Ltd., Rosh Ha'ayin (IL)

( * ) Notice: Subject to any disclaimer, the term of this patent is extended or adjusted under 35 U.S.C. 154(b) by 35 days.

(21) Appl. No.: 16/698,074

(22) Filed: Nov. 27, 2019

(65) Prior Publication Data
US 2020/0187760 A1 Jun. 18, 2020

Related U.S. Application Data

(63) Continuation of application No. 16/413,310, filed on May 15, 2019, now Pat. No. 10,492,670.

(60) Provisional application No. 62/781,035, filed on Dec. 18, 2018.

(51) Int. Cl.
| | |
|---|---|
| *A61B 1/015* | (2006.01) |
| *A61B 1/05* | (2006.01) |
| *A61B 1/06* | (2006.01) |
| *A61B 1/227* | (2006.01) |
| *A61F 11/00* | (2006.01) |

(Continued)

(52) U.S. Cl.
CPC ............... *A61B 1/015* (2013.01); *A61B 1/05* (2013.01); *A61B 1/0676* (2013.01); *A61B 1/227* (2013.01); *A61F 11/004* (2013.01); *A61M 1/7411* (2021.05); *A61M 1/842* (2021.05); *A61B 2017/00438* (2013.01); *A61B 2217/005* (2013.01)

(58) Field of Classification Search
CPC ..... A61B 1/012; A61B 1/015; A61B 1/00098; A61B 1/127; A61B 1/227; A61B 1/2275
See application file for complete search history.

(56) References Cited

U.S. PATENT DOCUMENTS

| | | |
|---|---|---|
| 3,643,563 A | 2/1972 | Nobusawa |
| 3,643,653 A | 2/1972 | Takahashi et al. |
| 4,641,663 A | 2/1987 | Juhn |

(Continued)

FOREIGN PATENT DOCUMENTS

WO WO2016108229 7/2016

OTHER PUBLICATIONS

International Search Report and Written Opinion for Application No. PCT/IB2019/001331 dated May 8, 2020.

*Primary Examiner* — Matthew J Kasztejna
(74) *Attorney, Agent, or Firm* — Merchant & Gould P.C.

(57) ABSTRACT

A device for visualizing and providing suction for a surgical procedure in an ear may include a handle, a main shaft extending from the handle, an imaging sensor at a distal end of the main shaft, a light source at the distal end of the main shaft, and a suction shaft extending from the handle. The device may also include a spring coupled with the suction shaft and/or the handle, such that when the suction shaft is advanced in a distal direction and then released, the suction shaft retracts automatically. The suction shaft may have a distal curved portion, and the device may have a thumb depress portion that allows a user to spin the suction shaft to suction in different directions. Some embodiments may include a suction shaft with a sharp distal tip that is configured for placing an ear tube in the tympanic membrane.

14 Claims, 32 Drawing Sheets

(51) Int. Cl.
*A61M 1/00* (2006.01)
*A61B 17/00* (2006.01)

(56) References Cited

U.S. PATENT DOCUMENTS

| | | | |
|---|---|---|---|
| 4,766,886 A * | 8/1988 | Juhn | A61B 1/227 600/200 |
| 5,152,278 A | 10/1992 | Clayman | |
| 5,667,473 A | 9/1997 | Finn et al. | |
| 5,916,150 A * | 6/1999 | Sillman | A61B 1/227 600/184 |
| 6,640,121 B1 * | 10/2003 | Telischi | A61B 5/283 600/379 |
| 7,789,825 B2 | 9/2010 | Nobis et al. | |
| 8,414,473 B2 | 4/2013 | Jenkins et al. | |
| 9,968,340 B2 | 5/2018 | Zinnanti | |
| 10,492,670 B1 | 12/2019 | Bendory et al. | |
| 2002/0019583 A1 * | 2/2002 | Elliott | A61B 1/00087 600/200 |
| 2003/0164952 A1 | 9/2003 | Deichmann et al. | |
| 2003/0171655 A1 * | 9/2003 | Newman | A61B 5/0059 600/200 |
| 2005/0277954 A1 | 12/2005 | Smith et al. | |
| 2006/0206118 A1 | 9/2006 | Kim et al. | |
| 2007/0167918 A1 * | 7/2007 | Reed | A61M 1/0064 604/187 |
| 2007/0293726 A1 | 12/2007 | Goldfarb et al. | |
| 2008/0021280 A1 | 1/2008 | Suzuki | |
| 2008/0167527 A1 | 7/2008 | Slenker et al. | |
| 2008/0294235 A1 | 11/2008 | Bendory et al. | |
| 2012/0059224 A1 * | 3/2012 | Wellen | A61B 1/227 600/200 |
| 2012/0253125 A1 | 10/2012 | Slenker et al. | |
| 2014/0012083 A1 | 1/2014 | Chin | |
| 2016/0073855 A1 | 3/2016 | Farr et al. | |
| 2016/0367404 A1 * | 12/2016 | Shomo | A61B 1/015 |
| 2017/0055811 A1 | 3/2017 | Germain et al. | |
| 2017/0239091 A1 * | 8/2017 | Franz | A61B 1/00052 |
| 2017/0258312 A1 | 9/2017 | Zhou et al. | |
| 2017/0265879 A1 | 9/2017 | Washburn, II et al. | |
| 2017/0280985 A1 | 10/2017 | Koda et al. | |
| 2017/0296388 A1 * | 10/2017 | Gaynes | A61B 1/227 |
| 2018/0125345 A1 * | 5/2018 | Rebella | A61B 1/00094 |
| 2019/0015254 A1 | 1/2019 | Bendory et al. | |
| 2020/0288962 A1 | 9/2020 | Bendory et al. | |

* cited by examiner

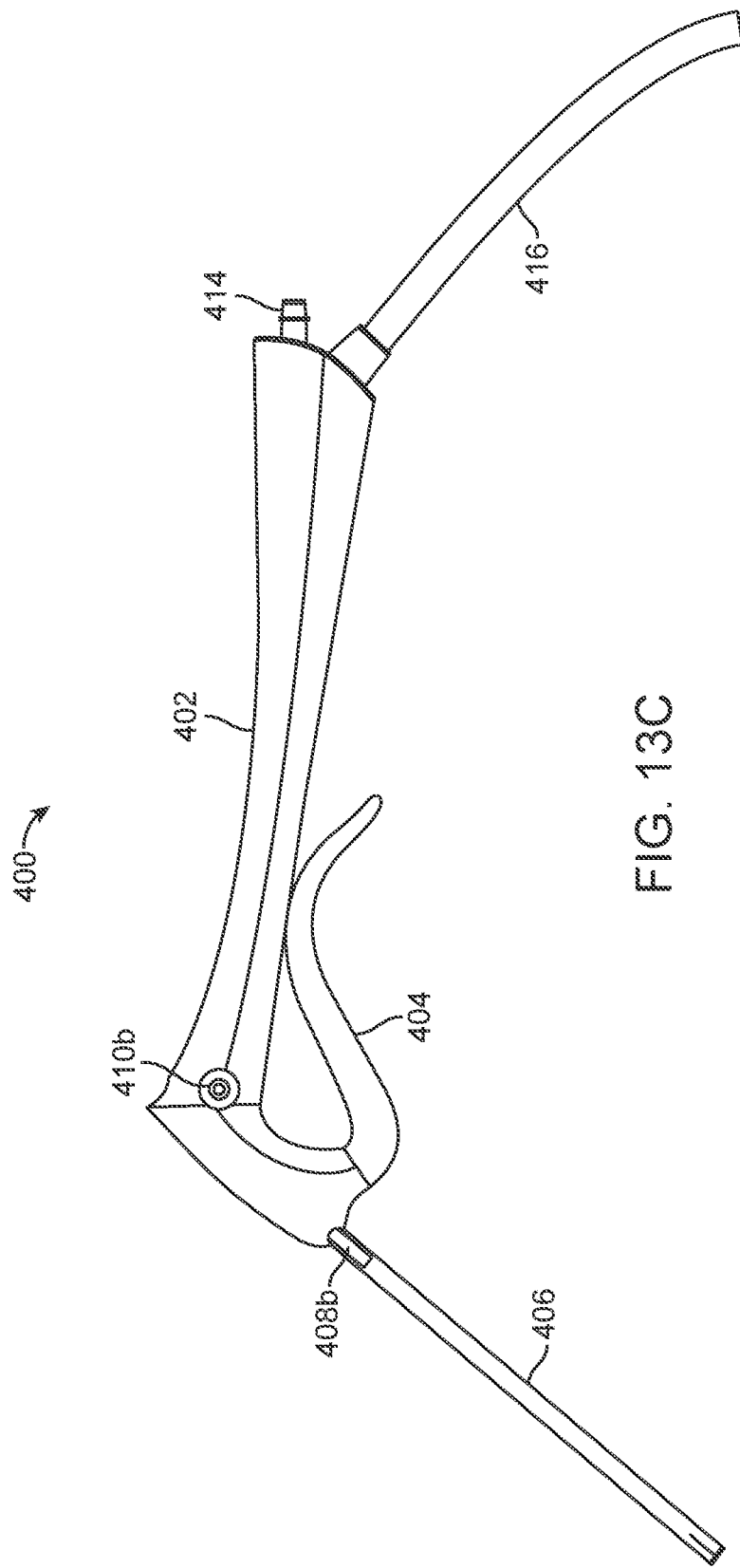

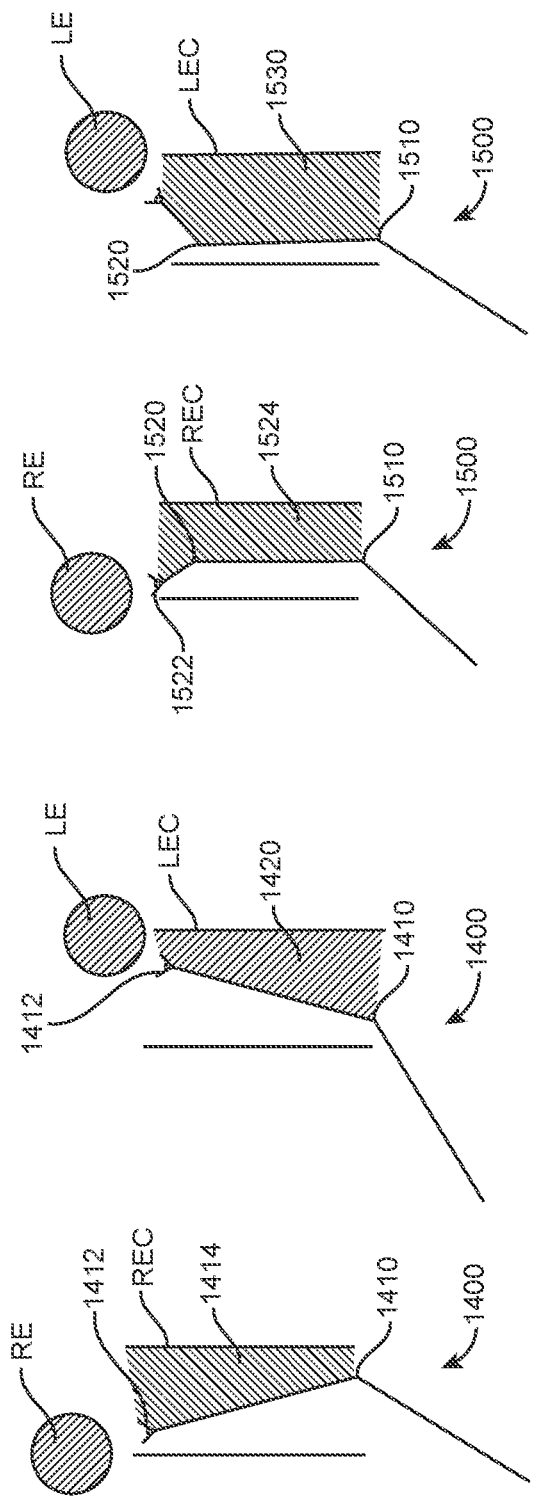

EAR VISUALIZATION AND TREATMENT SYSTEM

CROSS-REFERENCE TO RELATED APPLICATIONS

This application is a continuation of U.S. application Ser. No. 16/413,310, filed May 15, 2019, now U.S. Pat. No. 10,492,670, which claims the benefit of U.S. Provisional Patent Application No. 62/781,035, filed Dec. 18, 2018, both entitled, "Ear Visualization and Treatment System." The disclosure of this priority application is hereby incorporated by reference in its entirety into the present application.

BACKGROUND

Middle ear surgery is performed on patients for a number of different reasons, most commonly for chronic recurring ear infections. When performing middle ear surgery, the ear, nose and throat (ENT) surgeon (or "otolaryngologist") typically visualizes the middle ear and the surgical procedure in one of two ways. In some cases, the surgeon uses a microscope, positioned in front of the surgeon's eyes, and she typically uses her non-dominant hand to hold a suction device and her dominant hand to hold a surgical tool. In other cases, the surgeon uses a handheld endoscope to visualize the middle ear. The use of a handheld endoscope is problematic in several different ways.

First, standard endoscopes have long shafts and are not made for use in the ear. When the ENT surgeon uses an endoscope in the ear, he has to hold the handle of the scope up in the air, over the patient's head, with the surgeon's hand suspended in the air, unsupported. This factor alone is problematic, because if the surgeon accidentally moves his unsupported hand during surgery, he could very easily move the distal end of the endoscope in a way that could damage the tympanic membrane or one or more of the delicate structures of the middle ear.

Second, compounding on the first issue, endoscopes are generally much heavier than the small, thin surgical tools used in middle ear procedures. The surgeon thus has an ergonomic imbalance between a relatively heavy endoscope in her non-dominant hand and a relatively light surgical device in her dominant hand. This imbalance adds to the difficulty in stabilizing the endoscope. Additionally, holding a heavy endoscope suspended over the patient's head during a surgical procedure may quickly lead to arm and hand fatigue for the surgeon.

Third, since the surgeon is holding the endoscope in one hand, that hand is no longer free to hold a suction device or a surgical tool. Thus, when an endoscope is used for visualization, the surgeon cannot use a suction device and visualize the inside of the ear at the same time.

Fourth, standard endoscopes have straight shafts, so the surgeon must hold the endoscope in a direct line straight back from the patient's ear. This straight-line position makes it impossible, or at least incredibly challenging, to use an endoscope and a microscope in the same surgical procedure, since the position of the endoscope is directly in the path of vision of the microscope. This is a drawback, because in some procedures an ENT surgeon would like to be able to switch back and forth quickly and easily between viewing with a microscope and viewing with an endoscope. It is also challenging for a surgeon to manipulate multiple tools with straight shafts held in two hands during an ear surgery procedure, because the hands must be held very close together (due to the small diameter of the ear canal), and the tools tend to bump into one another as the surgeon manipulates them to perform the procedure.

For at least these reasons, it would be advantageous to have an improved system and method for ear visualization. Ideally such a system and method would be easy to use, allow for good visualization of the ear, and be compatible with use of other ear surgery devices. At least some of these objectives will be addressed in this disclosure.

BRIEF SUMMARY

This disclosure describes various embodiments of an ear endoscope device, system and method for visualizing an ear surgery procedure. In some embodiments, the ear endoscope device includes a handle, a main visualization shaft that holds a visualization component (e.g., a camera), and a tool attachment mechanism for coupling a surgical tool with the ear endoscope. Some embodiments also include the surgical tool itself. Specifically, several embodiments include a visualization component and a suction component, which work together as one device. The suction component (or other tool in alternative embodiments) may be coupled with the visualization component in a number of different ways, such as by a sheath, via one or more tubes or lumens, through the main visualization shaft, etc.

The device is configured to be held in, and operated with, one hand, and it is short enough and thin enough to be advanced easily into the ear canal and to allow the surgeon to rest her hand on the patient's head during the ear procedure while holding the device, which surgeons often do with their tool-holding hand in ear surgery procedures for stability. In various embodiments, the camera may be free to roll (or "spin") about its own axis within a sheath, the camera may be free to rotate around the longitudinal axis of the suction device within the sheath, and/or the attached suction device or other surgical tool may be free to spin around the camera and/or around its own axis.

In one aspect of the disclosure, a device for visualizing and providing suction for a surgical procedure in an ear may include a handle, a main shaft extending from the handle and defining a longitudinal axis, an imaging sensor at a distal end of the main shaft, a light source at the distal end of the main shaft, a suction shaft extending from the handle parallel to the longitudinal axis of the main shaft, and a spring coupled with the suction shaft and/or the handle, such that when the suction shaft is advanced in a distal direction and then released, the suction shaft retracts automatically. Some embodiments may further include a thumb depress member coupled with a proximal end of the suction shaft, where the spring is disposed over a proximal portion of the suction shaft, between a top of the handle and a bottom of the thumb depress member.

In some embodiments, the suction shaft includes a straight proximal portion that extends parallel to the longitudinal axis of the main shaft and a distal curved portion, where the suction shaft is coupled with the handle such that it can spin and thus cause the distal curved portion to point in different directions. Such an embodiment may further include a thumb depress member coupled with a proximal end of the suction shaft. Optionally, a surface feature may be included on a top surface of the thumb depress member for facilitating a user spinning the thumb depress member to spin the suction shaft. In some embodiments, the device may also include a handle suction port on the handle, a free spin suction member disposed over a proximal portion of the suction shaft such that the free spin suction member does not spin when the suction shaft spins, a suction shaft suction port on the free spin suction member, and a suction tube connecting the handle suction port with the suction shaft suction port. In some embodiments, the free spin suction member houses two O-rings positioned above and below a hole in the suction shaft that communicates with the suction shaft suction port on the free spin suction member, and the O-rings and the free spin suction member form a seal with the suction shaft over the hole.

In various embodiments, the suction shaft has an outer diameter of no more than 1.1 millimeter. Some embodiments further include a suction shaft guide positioned on one side of the main shaft, where the suction shaft extends through the suction shaft guide. In some embodiments, the device includes a first suction shaft guide positioned on a first side of the main shaft, and a second suction shaft guide positioned on a second side of the main shaft, where the suction shaft may be passed through either the first suction shaft guide or the second suction shaft guide to provide suction on either side of the main shaft.

In some embodiments, the suction shaft includes a sharp distal tip for piercing a tympanic membrane, and the device further comprises a stop member on the suction shaft for preventing an ear tube positioned on the suction shaft from sliding proximally past the stop member along the suction shaft. In some embodiments, the handle is adjustable from a straight configuration to an angled configuration. Other embodiments may include a handle angle adjustment member removably attachable to the handle to adjust an angle by which the handle is held by a user.

In some embodiments, the suction shaft extends alongside the main shaft. Alternatively, the suction shaft may extend through the main shaft. The handle may include at least one suction tube port for attaching a suction tube between the handle and the suction shaft. The handle may also include at least one suction finger control port, configured to allow a user to control application of suction by placing a finger over the finger control port and releasing the finger from the finger control port. Additionally, the handle may include a finger loop configured to allow the device to be held by a single finger of the user. In one embodiment, the finger loop is configured to extend around a middle finger of one hand of the user, the device further includes a thumb depress member to be manipulated by the thumb of the same hand, and the handle further includes a suction control port configured to be covered by the index finger of the same hand.

In another aspect of the disclosure, a device for visualizing a surgical procedure on an ear may include a suction tube, a camera coupled with the suction tube in a side-by-side arrangement, and a sheath disposed around an outside of the suction tube and an outside of the camera to couple the suction tube and the camera together. In some embodiments, the sheath holds the camera and the suction tube in such a way that the camera is free to roll or spin about its own axis within the sheath, and the camera is also free to rotate about a longitudinal axis of the suction tube within the sheath. In some embodiments, the suction tube may have an outer diameter of no more than about 1.1 millimeters, and the camera may have an outer diameter of no more than about 2.5 millimeters. In some embodiments, for example, the sheath is disposed around the camera and the suction tube but is not fixedly attached to either one, so they are free to roll and rotate within the sheath. For example, the surgeon may want to roll the camera for image orientation and/or may want to rotate the camera around the suction tube for ergonomic reasons, such when moving the device from one hand to the other.

In some embodiments, the suction tube is rigid and includes a tubular portion with a distal suction end, a suction device attachment end opposite the distal suction end, and a bend in the tubular portion. In some embodiments, for example, the tubular portion is located about 40-100 millimeters from the distal suction end. In one embodiment, the bend in the tubular portion forms an angle of about 45 degrees, although other angles are possible in alternative embodiments. In some embodiments, the sheath is shorter than a distance from the distal suction end to the bend in the tubular portion, and the camera and the sheath are configured to slide along the tubular portion of the suction tube from a first position, in which a distal end of the camera is adjacent to the distal suction end of the tubular portion, and a second position, in which the distal end of the camera is proximal to the distal suction end. In some embodiments the suction tube is made of metal. In some embodiments, at least a portion of the camera may be flexible. In some embodiments, the sheath is made of a heat-shrink polymer.

In another aspect of the disclosure, a method for performing a surgical procedure on an ear of a patient involves holding a combined visualization and suction device in one hand and advancing a distal end of the combined visualization and suction device into the ear. The combined visualization and suction device may be the same as or similar to the one described immediately above, and it may have any or all of the features described above. The method also involves viewing using the camera to view inside of the ear, activating the suction tube inside of the ear, and performing the surgical procedure on the ear, using a surgical tool held in the hand that is not holding the combined visualization and suction device. The method may also involve using the activated suction tube of the device to hold and move one or more structures within the ear. The activated suction tube may alternatively or additionally be used to suction fluid from the ear.

In some embodiments, the method may further involve rolling the camera about its own longitudinal axis within the sheath. The method may also involve rotating the camera around a longitudinal axis of the suction tube within the sheath. In some embodiments, the method may involve additionally viewing the ear using a microscope. Optionally, the suction tube may include a bend, and the method may further involve holding the combined visualization and suction device outside of a direct line of sight between a surgeon's eyes and the ear. The method may also involve supporting the hand that is holding the combined visualization and suction device on the patient's head during the surgical procedure. Optionally, the method may involve supporting the hand that is holding the surgical tool on the patient's head during the surgical procedure.

In another aspect of the present disclosure, a device for visualizing a surgical procedure in an ear may include an ear endoscope and a coupler. The ear endoscope includes a handle, a shaft extending from the handle and having a bend with an angle of 90-155 degrees, an outer diameter of no more than 2.5 millimeters, and a length of 30-80 millimeters, an imaging sensor at a distal end of the shaft, and a light source. The coupler is attached to a side of the ear endoscope shaft for attaching a tool to the endoscope. In various embodiments, the surgical tool and the overall device may include any of the features described above. The surgical tool may be a suction device, as previously described, or alternatively it may be any other suitable tool, such as but not limited to a cutting device, a piercing device, an ear tube placement device, a seeker, tweezers or forceps.

In another aspect of the disclosure, a method for performing a surgical procedure in an ear of a patient may first involve attaching a tool to an ear endoscope in a side-by-side arrangement, using a coupler, where the ear endoscope includes a shaft with a bend and an outer diameter of no more than 2.5 millimeters. The method may further involve holding a handle of the ear endoscope in one hand, advancing a distal end of the ear endoscope into the ear with the tool attached, viewing an inside of the ear, using the ear endoscope, and using the tool attached to the ear endoscope to facilitate or perform at least part of the surgical procedure. The combined visualization and surgical tool device may be the same as, or similar to, the embodiment described above, and it may include any of the features described above.

In another aspect of the present disclosure, an ear endoscope device for use in a surgical procedure in an ear may include a handle, a visualization shaft extending from the handle, a tool guide extending from the handle parallel to the visualization shaft and configured to guide a tool into the ear with the visualization shaft, an imaging sensor at a distal end of the visualization shaft, and a light source. In one embodiment, the ear endoscope device may include at least one tool coupler on a side of the shaft, at least one suction shaft insertion port at or near a distal end of the handle, two side suction tube connection ports at or near the distal end of the handle, a rear suction tube connection port at or near a proximal end of the handle, and a suction lumen connecting the rear suction tube connection port to the two side suction tube connection ports. In various embodiments, the shaft and the handle may form an angle of between about 90 degrees and about 155 degrees. In some embodiments, the shaft may have an outer diameter of no more than about 2.5 millimeters and a length of between about 30 millimeters and about 80 millimeters.

In some embodiments, the ear endoscope further includes a suction device. The suction device may include a suction shaft for passing through the at least one suction shaft insertion port and the at least one tool coupler, a thumb depress member coupled with the suction shaft for allowing a user to advance the suction shaft, a side suction tube for attaching the suction shaft, via the thumb depress portion, to one of the two side suction tube connection ports, and a rear suction tube for connecting the rear suction tube connection port to a suction source. The suction device may further include a spring disposed over a proximal portion of the suction shaft, between the thumb depress member and the handle of the ear endoscope. The spring may be configured to automatically retract the suction shaft relative to the shaft when the thumb depress portion is released. In some embodiments, an open one of the two side suction tube connection ports that is not attached to the side suction tube is configured to act as a finger operated suction control for controlling the application of suction force with a user's finger.

In some embodiments, the handle includes two suction shaft insertion ports and two tool couplers disposed on opposite sides of the shaft, where each of the two suction shaft insertion ports feeds into a corresponding one of the two tool couplers. In some embodiments, the handle includes a finger loop for facilitating holding the device with a user's finger under the handle. Alternatively, the handle may include any other finger hold shape or other ergonomic shape to facilitate gripping the device with one hand.

In another aspect of the present disclosure, a method for performing a surgical procedure in an ear canal of a patient may involve holding in one hand an ear endoscope with an attached suction device, advancing a distal end of the ear endoscope with the attached suction device into the patient's ear canal, depressing a thumb depress member of the suction device with a thumb of the hand, to advance a suction shaft of the suction device relative to a visualization shaft of the ear endoscope, applying suction in the ear canal with the suction device, and viewing an inside of the ear canal, using the ear endoscope. In one embodiment, applying suction in the ear canal involves applying a finger of the hand to an open suction control opening on the handle.

In some embodiments, the method also involves releasing the thumb depress portion to allow a spring on the suction shaft to expand to cause the suction shaft to retract relative to the shaft of the ear endoscope. In some embodiments, depressing the thumb depress member causes the suction shaft to advance through a suction shaft insertion port on a handle of the ear endoscope and through a tool coupler attached to the shaft of the ear endoscope. The spring may be disposed over the suction shaft, between the thumb depress member and the handle. The method may optionally also involve supporting the hand that is holding the ear endoscope on the patient's head during the surgical procedure.

These and other aspects and embodiments are described in further detail below, in relation to the attached drawing figures.

BRIEF DESCRIPTION OF THE DRAWINGS

FIGS. 13A-13C are right/rear perspective, left/rear perspective and left side views, respectively, of an ear endoscope device, according to one embodiment;

FIGS. 27A and 27B are diagrammatic illustrations of an ear visualization/suction device of the present application, shown in an orientation as if the device were being held in a left hand while inserted into a right ear (FIG. 27A) and a left ear (FIG. 27B), according to one embodiment; and FIGS. 28A and 28B are diagrammatic illustrations of an ear visualization/suction device of the present application, shown in an orientation as if the device were being held in a left hand while inserted into a right ear (FIG. 28A) and a left ear (FIG. 28B), according to an alternative embodiment.

DETAILED DESCRIPTION

Figure 1:
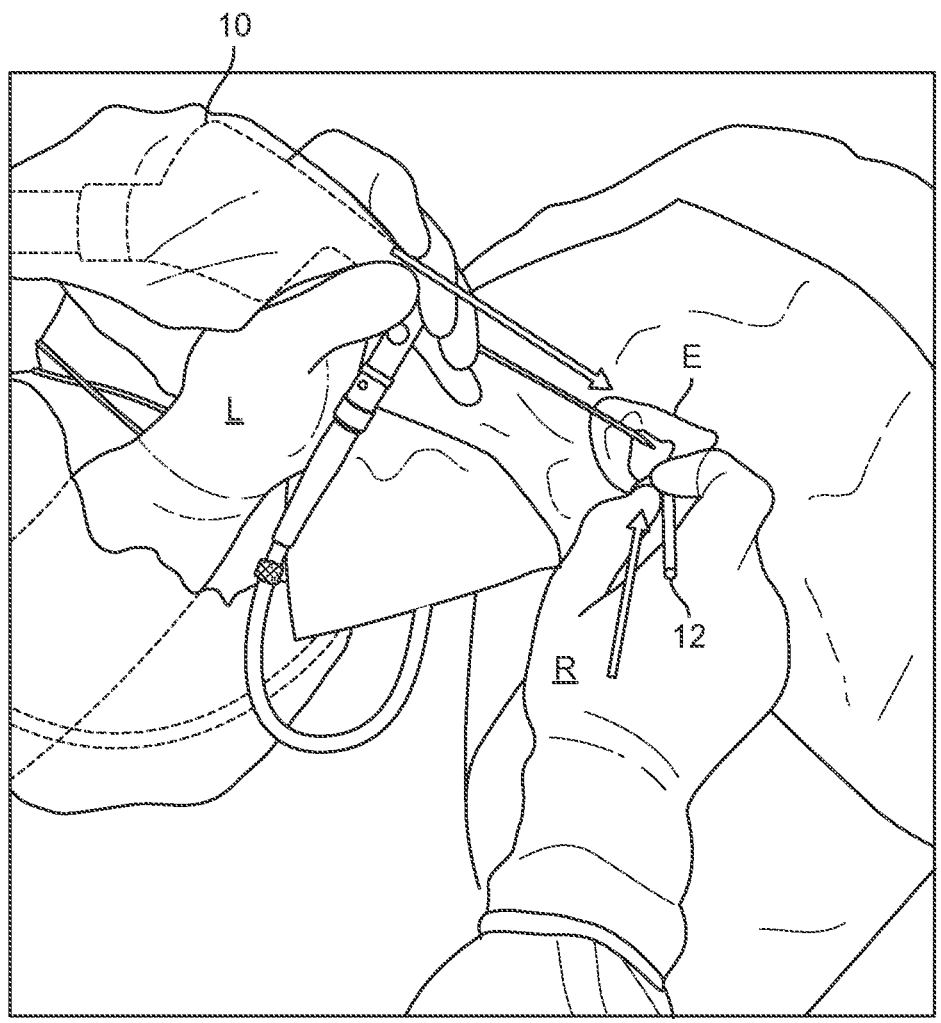
FIG. 1 is a perspective view of a surgeon's hands and a surgical field, including a patient's ear, illustrating how a prior art endoscope and surgical tool are typically held.

In general, the embodiments described herein are directed to a device, system and method for visualizing an ear surgery procedure. The ear visualization device generally includes an ear endoscope (or "camera"), with an attachment mechanism for attaching an additional tool to the endoscope. Oftentimes, the additional tool is a suction device, so the device provides for visualization and suction with one device, held in one hand. In alternative embodiments, however, any of a number of different tools may be attached to the endoscope, in addition to or instead of a suction device. In some embodiments, the attachment mechanism for attaching the additional tool is built into the endoscope. Alternatively, the attachment mechanism may be a separate coupler or sheath, which attaches to the shaft of the ear endoscope and allows any of a number of different types of surgical tools to be attached to the endoscope in a side-by-side arrangement. In yet other embodiments, visualization and suction may be integrated into the device. The ear visualization system may include the ear endoscope along with a separate attachment mechanism, a light source for the endoscope, a video monitor for displaying images captured by the endoscope and/or any other suitable components. In some embodiments, the system may also include a suction device or other surgical tool. In other embodiments, the ear endoscope device or system may be provided by itself, and may be used with one or more optional, stand-alone tools.

As mentioned immediately above, in some embodiments, the attachment mechanism is a separate piece, which may be removed from the endoscope shaft. In such embodiments, the endoscope and the coupler may be referred to as a "system," due to the combination of two different devices. In alternative embodiments, the coupler may be integral with, or permanently attached to, the endoscope shaft, in which case the endoscope with coupler may be referred to as a "device." In any case, use of the terms "system" and "device" herein should not be interpreted as limiting the scope of the invention.

In some embodiments, the device may include an endoscope and a suction tube that also operates as an ear tube placement device. The distal tip of the suction/ear tube placement component may have a sharp distal tip to pierce the tympanic membrane, and the device may also include a stop for preventing the ear tube from sliding proximally up the suction/ear tube placement component. This device embodiment is described in further detail below.

The shaft of the ear endoscope and whatever surgical tool it is used with may have very small diameters, so the distal end of the combined device fits easily into an ear canal, for helping visualize and perform an ear surgery procedure. In some embodiments, the coupler surrounds part of the endoscope shaft and part of the surgical tool in such a way that the shaft can rotate about a longitudinal axis of the tool and can also roll (or "spin") about its own longitudinal axis.

In one embodiment, described in detail below, the surgical tool is a suction tube device. In alternative embodiments, however, the tool may be any suitable, small-diameter tool, such as but not limited to a cutting device, a piercing device, an ear tube placement device, a seeker, tweezers, forceps, a speculum, a grasper, or a curette. In the description below of the suction embodiment, the fact that any other suitably sized surgical tool may be substituted for the suction device will not be repeated with the description of every embodiment. Similarly, the devices and methods described below for use in an ear surgery procedure may be used or adapted for use in any other suitable surgical procedure. This, too, will not be repeated with the description of every embodiment.

Although the following description is focused on use of the devices, systems and methods for visualizing and facilitating ear surgery procedures, the same embodiments may be used, or adapted for use, in any other suitable procedures and parts of a human or animal body. Therefore, the invention is not limited to use in the ear.

Referring now to FIG. 1, a prior art method for performing an ear surgery using a standard endoscope 10 is illustrated. The figure shows a surgical field, with the patient's ear E exposed for the procedure. The surgeon is holding the endoscope 10 in his left hand L and a surgical tool 12 in his right hand. Due to the length of the endoscope 10, the surgeon has to hold his left hand L up in the air, suspended over the patient, in order to hold the handle of the endoscope 10. As mentioned previously, this can be very awkward and potentially dangerous to the tympanic membrane and/or structures of the middle ear, especially in longer procedures where the surgeon's left arm and left hand L get fatigued. Additionally, the surgeon does not have a free hand to hold a suction device or other surgical tool, since both of the surgeon's hands are occupied. To have suction in this scenario, a nurse or other assistant would have to hold the suction device in the patient's ear.

Figure 2:
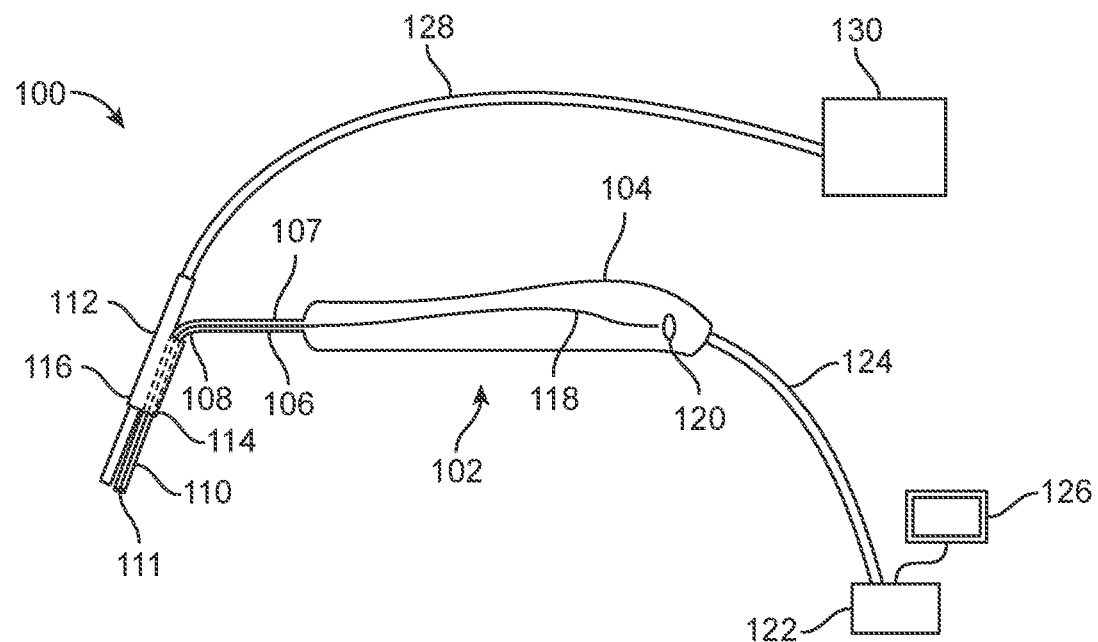
FIG. 2 is a side view of an ear visualization system, shown with a suction device, according to one embodiment.

Referring to FIG. 2, an ear surgery visualization system 100, according to one embodiment, may include an ear endoscope 102 and a coupler 112. Also pictured in FIG. 2 is a suction device 128, which is not necessarily part of the system 100, but which is shown in the figure for illustrative purposes. In alternative embodiments, the suction device 128 may be replaced by any other suitable surgical tool, such as the ones listed previously.

The ear endoscope 102 includes a handle 104, a shaft 106 and a processor 122, which may also act as a light source. The shaft 106 includes a proximal portion 107, a bend 108 and a distal portion 110, ending in a distal tip 111. The endoscope 102 also includes a light source 120 in the handle 104, and light fibers 118 that carry the light from the light source 120, through the shaft 106, to the distal tip 111. A camera on a chip (described more fully below) may be positioned at the distal tip 111, to acquire images of the ear. The system 100 may also include a video monitor 126, although optionally the video monitor 126 may be a separate component that is not part of the system 100. In another embodiment, the processor 122 and video monitor 126 may be combined in one unit.

The shaft 106 of the endoscope 102 may have a total length of about 30 millimeters to about 80 millimeters and an outer diameter of less than about 2.5 millimeters. In some embodiments, the outer diameter of the shaft 106 may be continuous along its length. Alternatively, the outer diameter of the distal portion 110 may be smaller than the outer diameter of the proximal portion 107. The bend 108 may form an angle between the proximal portion 107 and the distal portion 110 of between about 90 degrees and about 155 degrees. The handle 104 may be very small and lightweight, compared to typical endoscope handles. In fact, the handle 104 may be shaped to have a comfortable pencil grip, so the surgeon may hold and manipulate the ear endoscope 102 like a pencil. Ear endoscope 102 may also include a cable 124, attaching the handle 104 to the processor 122.

The coupler 112 includes an endoscope attachment portion 114 and a tool attachment portion 116. In some embodiments, each of the two portions 114, 116 is shaped as a tube or a semicircular tube. In some embodiments, the endoscope attachment portion 114 and the tool attachment portion 116 may have the same diameter. Alternatively, they may have different diameters. For example, in some embodiments the endoscope attachment portion 114 has a larger diameter than that of the tool attachment portion 116. The coupler 112 may be permanently attached to the shaft 106, or it may be removable, according to different alternative embodiments. The coupler 112 may be attached to the distal portion 110 of the shaft 106, as shown. Alternatively, the coupler 112 may be attached to the proximal portion 107, for example if the shaft 106 is straight, or of the coupler 112 follows the bend 108 in the shaft 106.

The weight, size and feel of the ear endoscope 102 may be similar to that of other ear surgery tools. This makes it more comfortable for the surgeon to hold and prevents an imbalance between the ear endoscope 102 and other tools. The surgeon may hold the handle 104 with a pencil grip and may rest her hand and/or the handle 104 on the patient's head during the procedure. In order to achieve this desired weight, size and feel, any suitable materials may be used for the various parts of the ear visualization system 100. For example, in one embodiment, the handle 104 may be made of any suitable lightweight plastic, and the shaft 106 may be made of any suitable metal, such as stainless steel. Alternatively, the handle 104 may be made of a lightweight metal. The coupler 112 may be made of plastic or metal, for example. Any suitable, medically safe materials may be used.

As mentioned above, a suction device 128 is illustrated in FIG. 2, attached to the shaft 106 of the endoscope 102 via the coupler 112, in a side-by-side arrangement. Any other tool may be substituted for the suction device 128, in alternative embodiments. The suction device 128 is also shown with a source of suction 130, which may be a separate component, wall suction, or any suitable suction source. The suction tube portion of the suction device 128 is flexible, at least along part of its length, and has a distal portion with an outer diameter that fits within the tool attachment portion 116 of the coupler. Various embodiments and features of a suction device 128 are described in further detail below.

Figure 3:
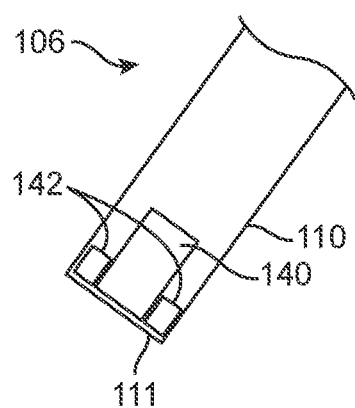
FIG. 3 is a close-up illustration of a distal portion of the ear endoscope shown in FIG. 2.

Referring now to FIG. 3, the distal portion 110 of the endoscope shaft 106 is illustrated in greater detail. At the distal end 111 of the shaft 106 are positioned an imaging sensor 140 and two light sources 142. The imaging sensor 140 may be any type of suitable sensor, such as a complementary metal-oxide semiconductor (CMOS) camera or any other "camera on a chip" type of device. The two light sources 142 (or alternatively any other number of light sources) may be light emitting diode (LED) lights, for example. These may be in addition to, or as an alternative to, the light source 120 shown in the handle 104 in FIG. 2. In other words, according to various embodiments, one or more light sources for the endoscope device 102 may be located in the handle 104, at the distal end 111 of the shaft 106, or both.

Figure 4:
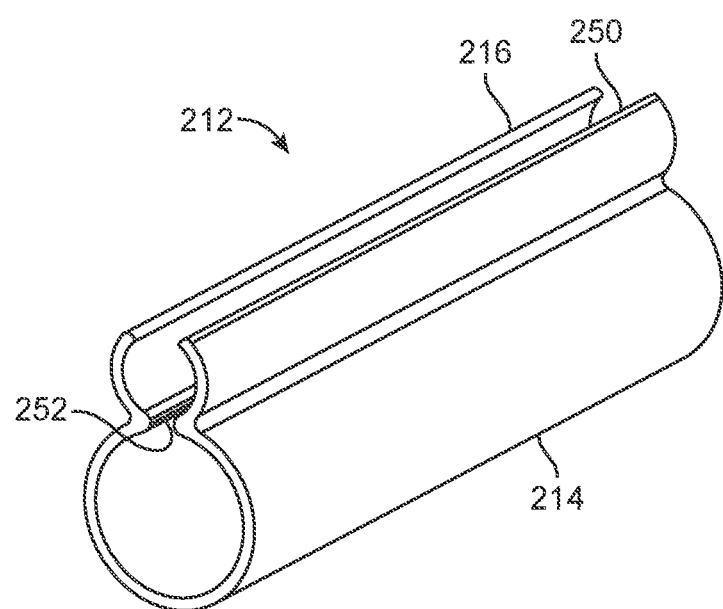
FIG. 4 is a perspective view of coupler for use with an ear visualization system, according to one embodiment.

FIG. 4 is a magnified view of an alternative embodiment of a coupler 212 for use with the ear endoscope 102. The coupler 212 includes an endoscope attachment portion 214, a tool attachment portion 216, a longitudinal top opening 250 in the tool attachment portion 216, and a longitudinal middle opening 252 between the endoscope attachment portion 214 and the tool attachment portion 216. In this embodiment the endoscope attachment portion 214 has a larger diameter than that of the tool attachment portion 216. The tool (not shown) may be inserted into the tool attachment portion 216 by pushing it down through the top opening 250 or by sliding it into the proximal end of the tool attachment portion 216 and advancing it distally. In the case where the tool is pushed through the top opening 250, the coupler 212 may flex outward slightly, by expanding at the two openings 250, 252, to accommodate the tool. In alternative embodiments, the endoscope attachment portion 214 and/or the tool attachment portion 216 may be formed as complete tubes, with circular cross-sections rather than semi-circular cross-sections. As mentioned above, the coupler may be made of any suitable material.

Referring to FIGS. 5A-5D, one embodiment of an ear surgery visualization device 20 is illustrated. In this embodiment, the visualization device 20, which may also be called "a combined visualization and suction device," includes a suction tube 22, a camera 30 and a coupler 38 (or "sheath") disposed around the suction tube 22 and the camera 30. The suction tube 22 has a distal end 24, a proximal end 26 for connecting with suction tubing connected to a suction source, and a bend 28 along its length. The camera 30 includes a distal portion 32, a proximal portion 36 and a distal end 34.

The suction tube 22 may be any standard or customized suction tube device. In various embodiments, the suction tube 22 may be rigid and may be made out of any suitable material, such as stainless steel or other biocompatible metal or plastic. The suction tube 22 will have an overall diameter and length to allow it to be advanced easily into the ear and to allow a surgeon to hold the visualization device 20 with one hand, resting on the patient's head, during the procedure. In some embodiments, for example, the suction tube 22 has an outer diameter, at least along the portion between the bend 28 and the distal end 24, of about 0.6 millimeter to about 1.1 millimeters. The bend 28 in the suction tube 22 is optional, and alternative embodiments may be straight. The bend 28 may be advantageous, however, because it allows the visualization device 20 to be held at an angle from the ear, so the hand holding the device 20 is not in the direct line of sight of the surgeon. This is especially advantageous in cases where the surgeon wants to use a microscope and the visualization device 20 in the same procedure, but it is also advantageous in keeping the suction tube 22 and the camera 30 out of the way of any surgical tools held in the surgeon's other hand. In various embodiments, for example, the bend 28 may be located about 40 millimeters to about 100 millimeters from the distal end 24 of the suction tube 22. In one embodiment, the bend may be about 60 millimeters from the distal end 24. In alternative embodiments of the device 20, where the camera 30 is combined with a different type of surgical tool rather than the suction tube 22, that surgical tool may also include the same or a similar bend.

The camera 30 may be any suitable, small-diameter camera for viewing an ear during an ear surgery procedure. In some embodiments, for example, the camera 30 may be a fiber optic camera or a complementary metal-oxide-semiconductor (CMOS) camera. As small-diameter cameras are well known, they will not be described in detail here. In some embodiments, at least the distal portion 32 of the camera 30 may be relatively rigid, so that the surgeon can easily roll it about its longitudinal axis and/or rotate it relative to the suction tube 22. In some embodiments, the camera 30 may include a bend, which may coincide with the bend 28 in the suction tube. The camera 30 may include CMOS sensors with a lens array. The sensors may be arrayed in a cube of between 0.6 mm by 0.6 mm and 1.0 mm by 1.0 mm, with overall length of up to 3 mm, in some examples. Alternative embodiments may include a fiber optic bundle for image capture, rather than CMOS. The light source for illumination may be LED at the distal tip 34 or fiber infused with light from a remote LED.

The cross-sectional shape of the camera 30 may vary in different embodiments (round, oval, square, rectangular, etc.), but in the embodiment shown the camera 30 has a round cross-sectional shape. This is advantageous for rolling and rotating the camera 30 within the coupler 38 and relative to the suction tube 22. The body of the camera 30 is made from a relatively rigid or at least semi-rigid material, such as stainless steel or plastic (e.g., thermoplastic). The length of the distal portion 32 may be, for example, about 5 mm to about 100 mm. In some embodiments, the distal portion 32 may be as long as the length of the suction tube 22 from its distal end 24 to the bend 28, which in one embodiment is about 60 mm. In various embodiments, the camera 30 and a light source may be integrated into a metal tube, overmolded with plastic, encapsulated in a polymer, or the like.

Figure 5A:
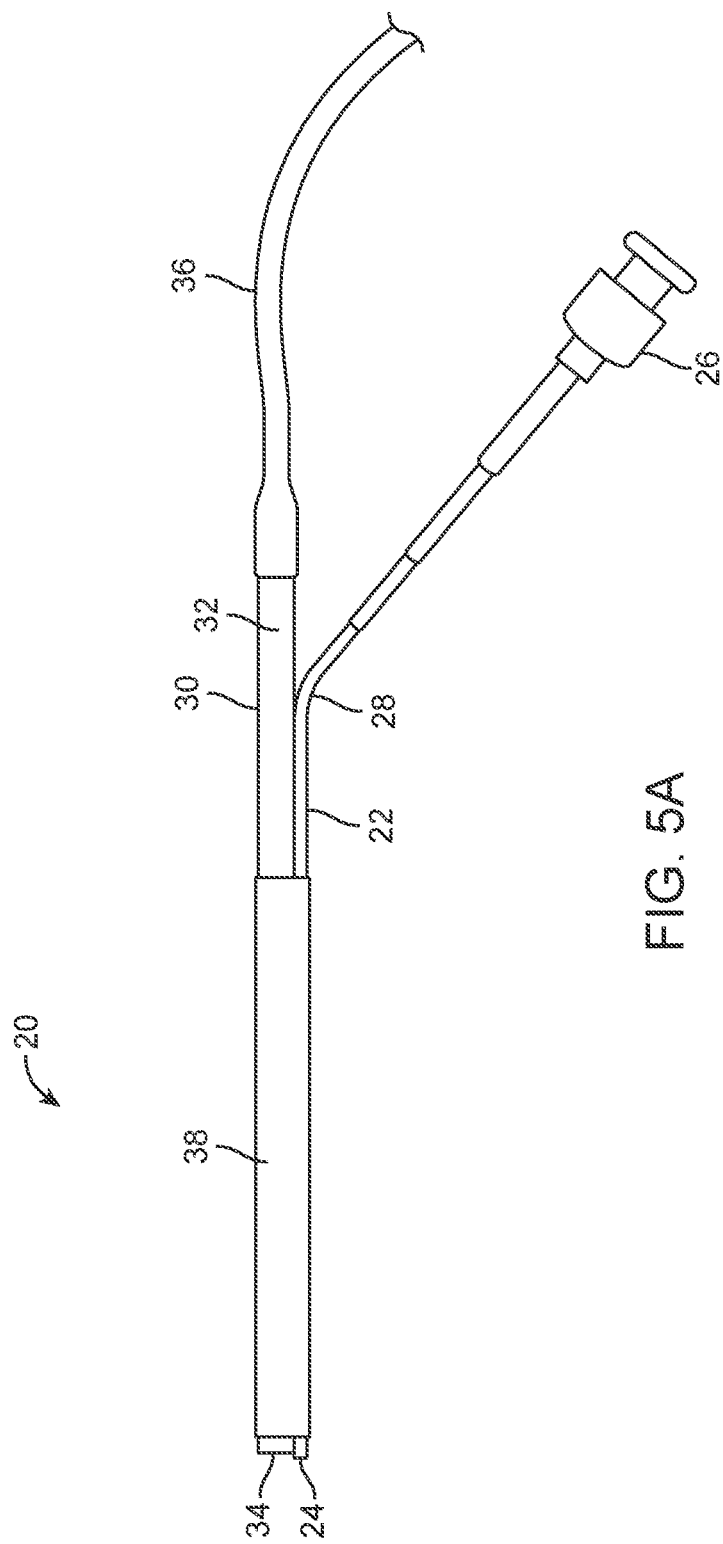
FIG. 5A is a side view of a combined visualization and suction device for use in ear surgery procedures, according to one embodiment.
Figure 5B:
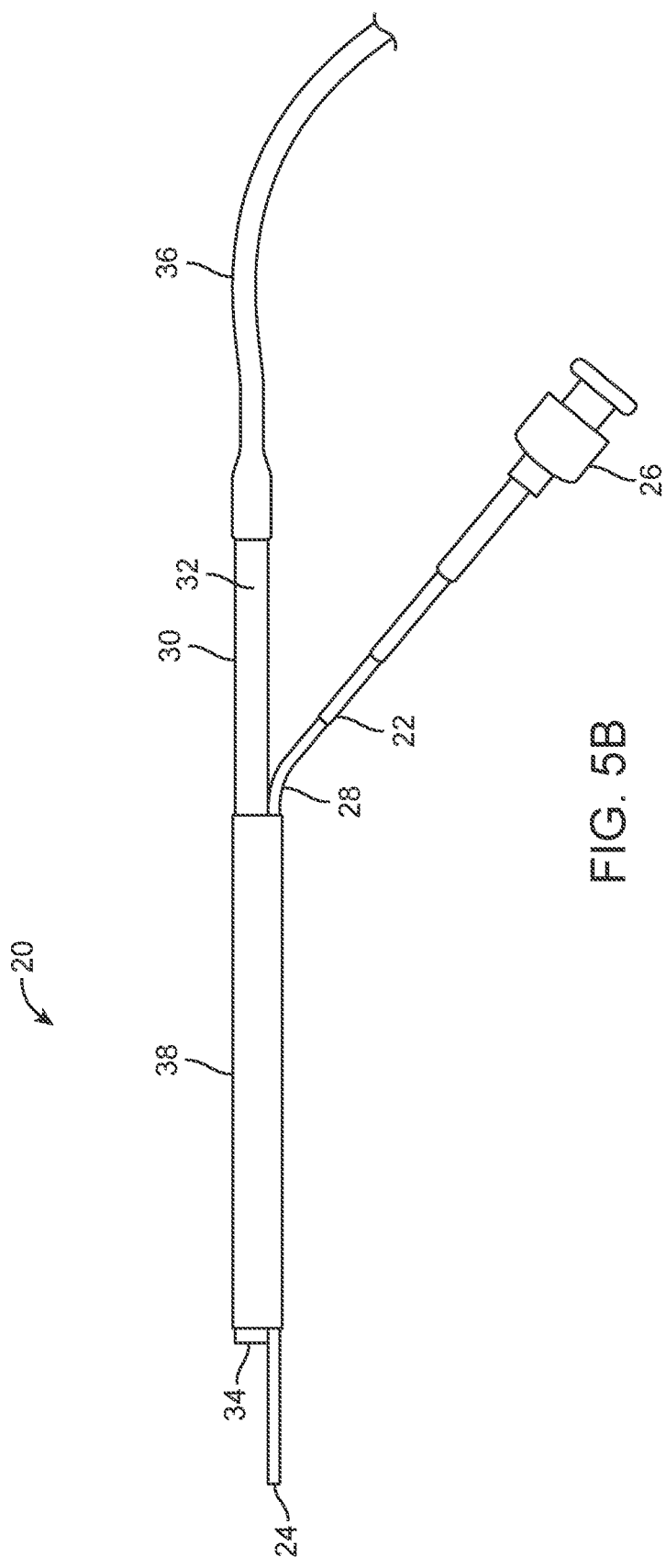
FIG. 5B is a side view of the visualization/suction device of FIG. 5A, with the suction component advanced distally, relative to the visualization component.

The coupler 38 may be any suitable material and have any suitable length, thickness and size, according to various embodiments. In one embodiment, the coupler 38 is formed as a tube of heat-shrink polymer wrap that surrounds distal portions of the suction tube 22 and the camera 30. The heat-shrink polymer may be polyethylene terephthalate (PET) in some embodiments, or may alternatively be any other suitable polymer, such as but not limited to a polyolefin, a polyimide or nylon. As illustrated in FIGS. 5A and 5B, in one embodiment, the coupler 38 is disposed about the suction tube and the camera 30 such that the suction tube 22 can advance (FIG. 5B) and retract (FIG. 5A), relative to the coupler 38 and the camera 30. For example, in some embodiments, the suction tube 22 can advance from a position where its distal end 24 is at or near the distal end 34 of the camera 30 (FIG. 5A) to a position where its distal end 24 is ahead of that of the camera 30 (FIG. 5B). In this embodiment, the camera 30 may also be able to slide forward and backward. In alternative embodiments, camera 30, suction tube 22 or both may be fixed to the inner surface of the coupler 38, such as by adhesive, thus reducing the amount of mobility of one or both components relative to the coupler 38.

Figure 5C:
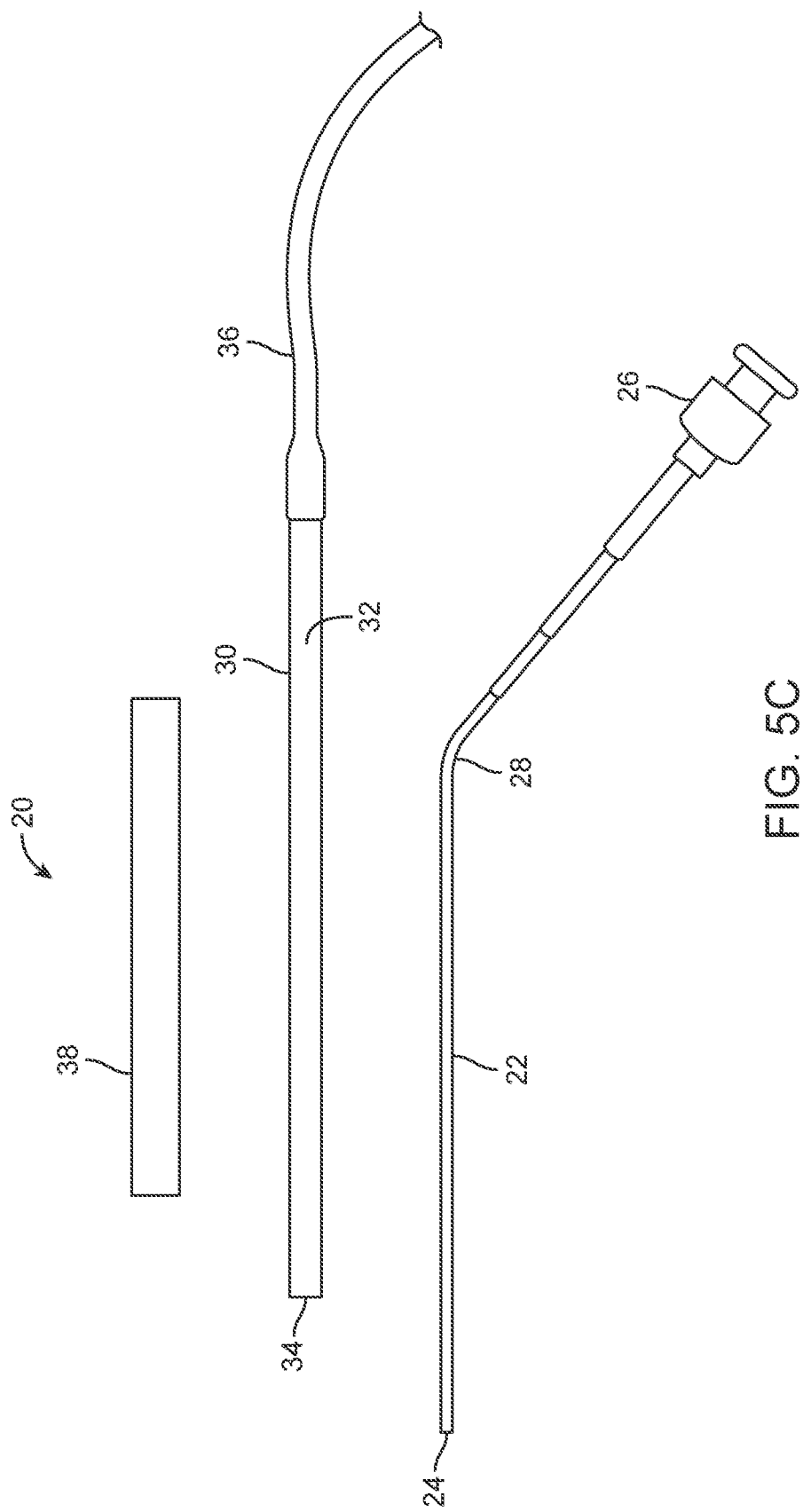
FIG. 5C is a side, exploded view of the visualization/suction device of FIGS. 5A and 5B.

FIG. 5C is an exploded view of the ear surgery visualization device 20, showing the suction tube 22, the camera 30 and the coupler 38 separate from one another. For assembly, the coupler 38 may be wrapped or slid over the suction tube 22 and the camera 30 in some embodiments.

Figure 5D:
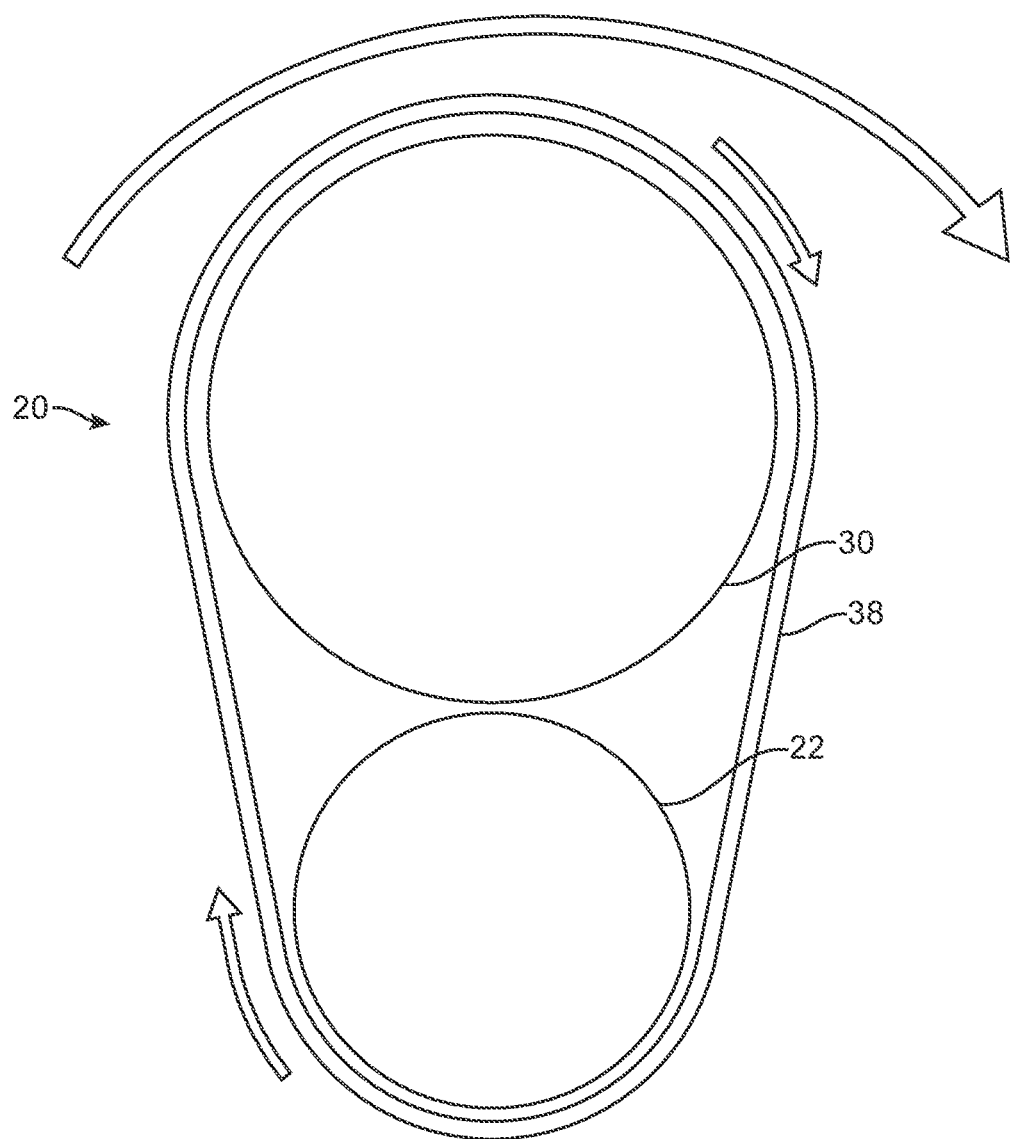
FIG. 5D is a front, end-on view of the shafts of the combined visualization and suction device of FIGS. 5A-5C.

FIG. 5D illustrates possible directions of movement of the camera 30, the suction tube 22 and the coupler 38, relative to one another. In some embodiments, the coupler 38 may be positioned around but not fixedly attached to the camera 30 and the suction tube 22, as described above. In addition to allowing the suction tube 22 and/or the camera 30 to advance longitudinally through the coupler 38, this configuration also allows the suction tube 22 and the camera 30 to roll about their own axes within the coupler 38 (two small hollow arrows around perimeter of coupler 38). Additionally, the camera 30 may be rotated around a longitudinal axis of the suction tube 22 (larger hollow arrow). The suction tube 22 may also be rotated around a longitudinal axis of the camera 30. This freedom of movement-rotation and rolling-allow the surgeon to adjust the orientation of the camera 30 and/or the suction tube 22 easily and quickly, without necessarily changing the orientation of both components. Again, however, in alternative embodiments the coupler 38 may be adhered or otherwise fixedly attached to either or both of the camera 30 and the suction tube 22.

Figure 6:
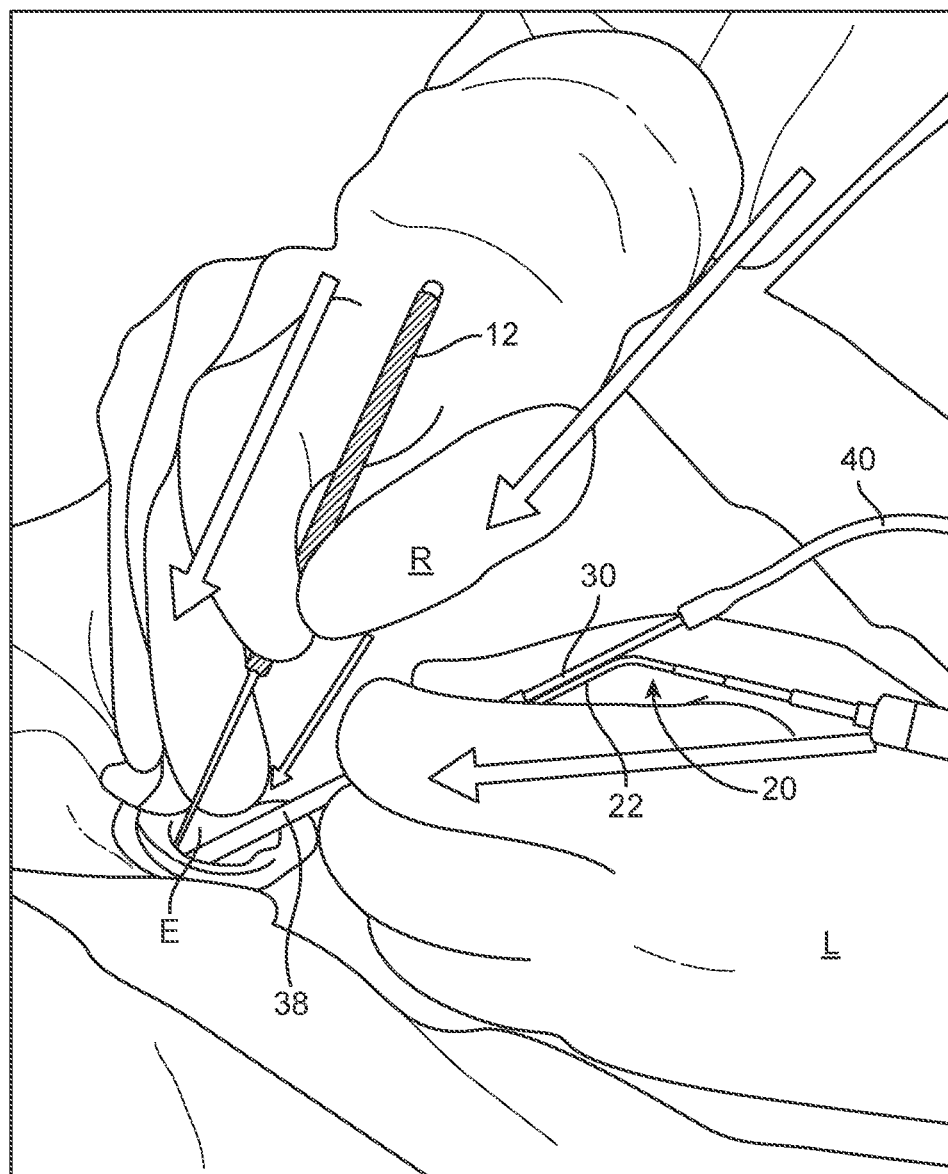
FIG. 6 is a perspective view of a surgeon's hands and a surgical field, including a patient's ear, illustrating how a combined visualization and suction device, according to one embodiment, may be held and used during an ear surgery procedure.

FIG. 6 shows a surgical field, including a patient's ear E, and the left hand L and the right hand R of a surgeon, performing a procedure on the ear E. The surgeon's left hand L is holding the ear surgery visualization device 20, as described above, which includes the suction tube 22 and the camera 30. The suction tube 22 is attached proximally to a suction hose 40, which in turn is attached to a source of suction (not shown). The surgeon's right hand R holds a surgical tool 12. As indicated by the large arrows on the figure, the surgeon's hands are approaching the ear E from two different angles, leaving a line of direct vision open from the surgeon's eyes to the patient's ear E (depicted by the middle/upper-right hollow arrow). This arrangement will allow a surgeon to visualize the surgical field using both a microscope and the camera 30, if desired. As also illustrated in FIG. 6, the ear visualization device 20 is sized and shaped such that the surgeon can rest her hand on the patient's head during the procedure. In performing the procedure, the surgeon may advance the device 20 into the ear E, suction out the ear E using the suction tube 22, visualize the ear E using the camera 30, and perform the procedure. Alternatively or additionally, the suction tube 22 may be used to hold onto and move one or more small anatomical structures of the ear, such as but not limited to the bones of the middle ear. Suction may also be used to hold different devices, such as an ear tube or ossicular prostheses. The device 20 is generally small enough that the camera 30 can be used to visualize the middle ear through a natural hole or incision in the tympanic membrane. These actions may be performed in any sequence and in any combination. In some embodiments, it may be possible for the surgeon to separate the camera 30 from the suction tube 22 during the ear surgery procedure, so they can be used separately.

In some embodiments, the ear surgery visualization device 20 may be used with another, different ear surgery visualization device (not shown). For example, the combined camera/suction tube device 20 may be held in the surgeon's non-dominant hand, and a combined camera/surgical tool device may be held in the surgeon's dominant hand. These two devices 20 may be used at the same time, thus acquiring two images of the ear. The views from the two cameras may be displayed on a single, split video screen, for example, with the right half marked 'R' and the left half marked 'L'. In all embodiments, the video screen may be separate and located above the patient's head and within the field of view of a microscope, so that the surgeon can view the surgical field through the microscope and look at the endoscopic view through the microscope as well, or simply switch from looking through the microscope to looking at the video screen. In another embodiment, it may be possible to digitally feed the endoscopic image into the microscope, so that the surgeon can view both of them through the microscope, or toggle between them by pressing a button, for example.

Figure 7:
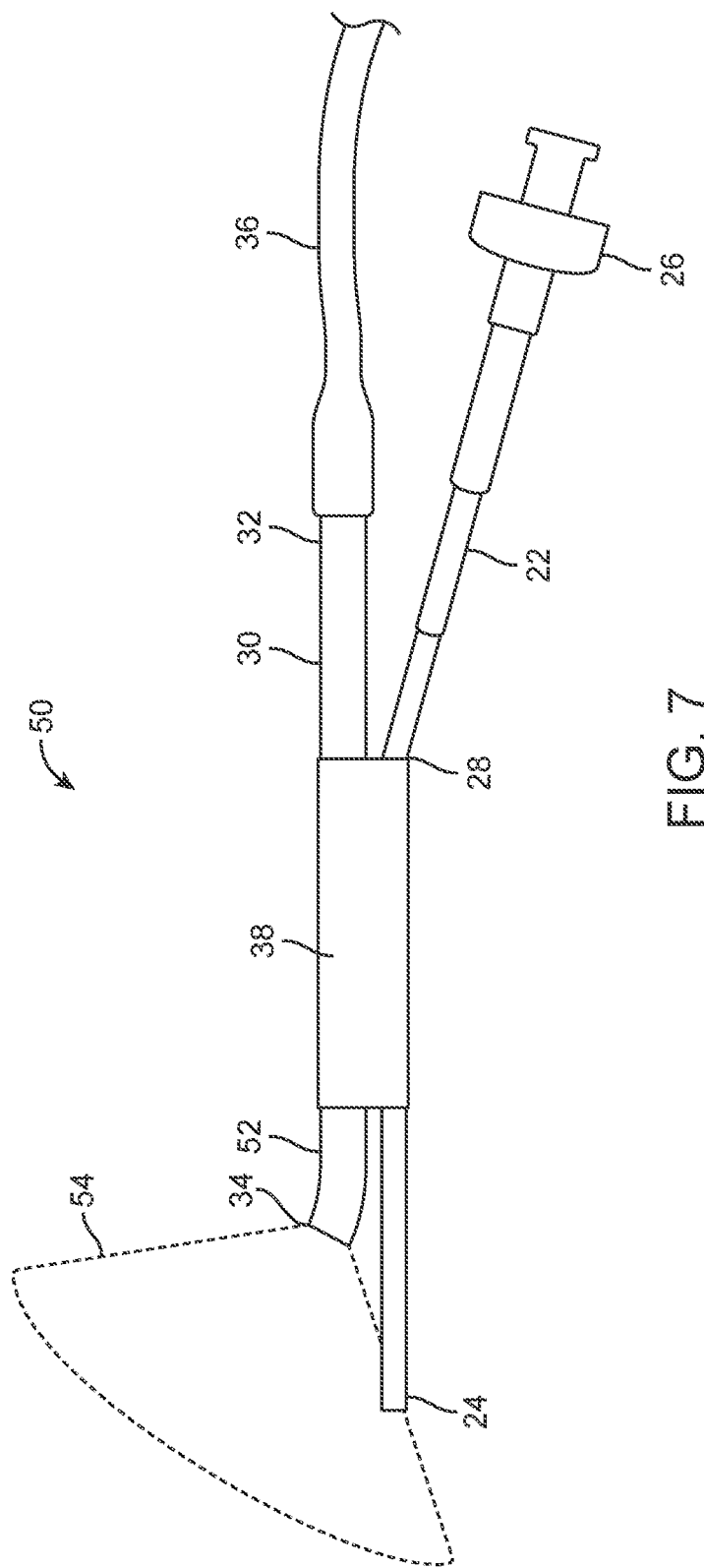
FIG. 7 is a side view of a combined visualization and suction device for use in ear surgery procedures, where the camera has a bend near its distal end, according to one embodiment.

Referring now to FIG. 7, an alternative embodiment of an ear surgery visualization/suction device 50 is illustrated. As mentioned above, in some embodiments, the suction tube 22 may be advanced, relative to the camera 30, as shown in FIG. 5B, such that the distal end 24 of the suction tube 22 is ahead of the distal end 34 of the camera 30. In embodiments where the distal portions of the suction tube 22 and the camera 30 are both straight and are connected in parallel with one another, the suction tube 22 may interfere with the field of view of the camera 30 in this configuration. The embodiment of the device 50 shown in FIG. 7 is configured to address that issue. In this embodiment, the distal portion 32 of the camera 30 includes a bend 52. This bend 52 orients the field of view 54 of the camera 30 at an angle, relative to the longitudinal axes of the suction tube 22 and the camera 30, so the suction tube 22 does not interfere with or limit the field of view 54. In various embodiments, the bend 52 may be located anywhere along the length of the camera 30, although in many embodiments it will be located near the distal end 34, so that it is distal to the distal end of the coupler 38.

Figure 8:
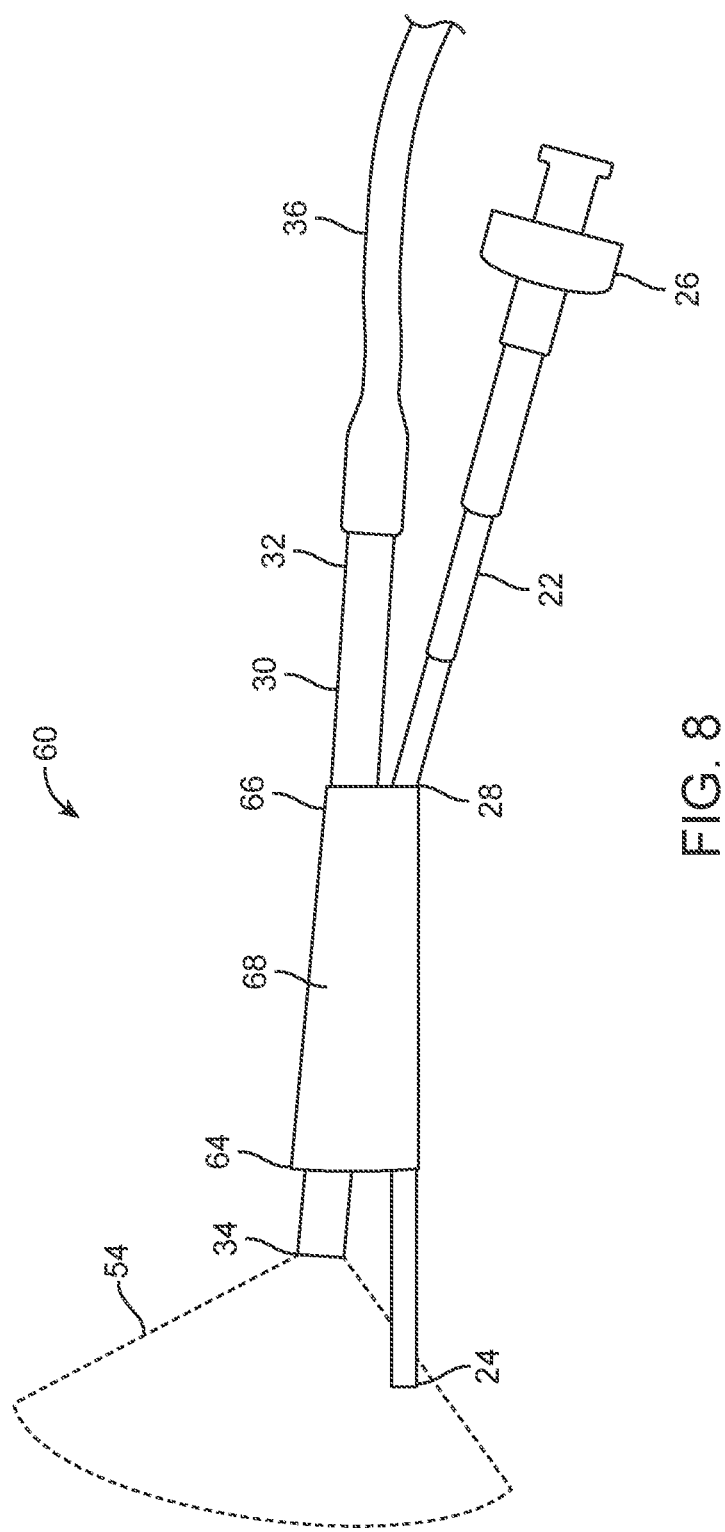
FIG. 8 is a side view of a combined visualization and suction device for use in ear surgery procedures, where the sheath couples the camera and suction tube together at an angle relative to one another, according to another embodiment.

Referring now to FIG. 8, another alternative embodiment of an ear surgery visualization/suction device 60 is illustrated. This embodiment is alternative way of addressing the issue of the suction tube 22 cutting off part of the field of view 54 of the camera. In this embodiment, the sheath 68 has a wider distal end 64 and a narrower proximal end 66. Thus, the sheath 68 couples the camera 30 and the suction tube 22 together such that they are oriented at an angle relative to one another. In other words, they are not parallel with one another. As with the previous embodiment, this helps prevent the field of view 54 of the camera 30 from being limited by the suction tube 22.

Figure 9A:
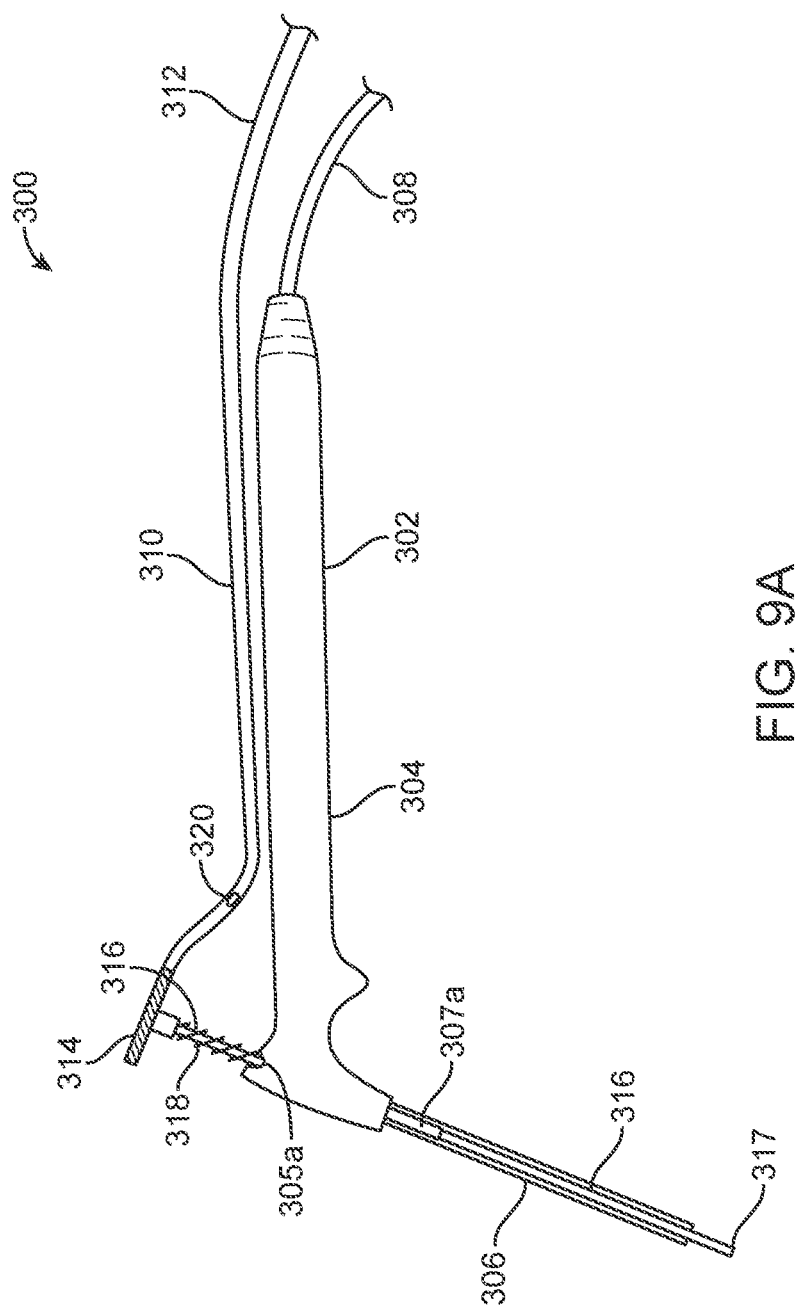
FIGS. 9A-9C are side, front and exploded views, respectively, of a combination visualization and suction device, according to an alternative embodiment.
Figure 9B:
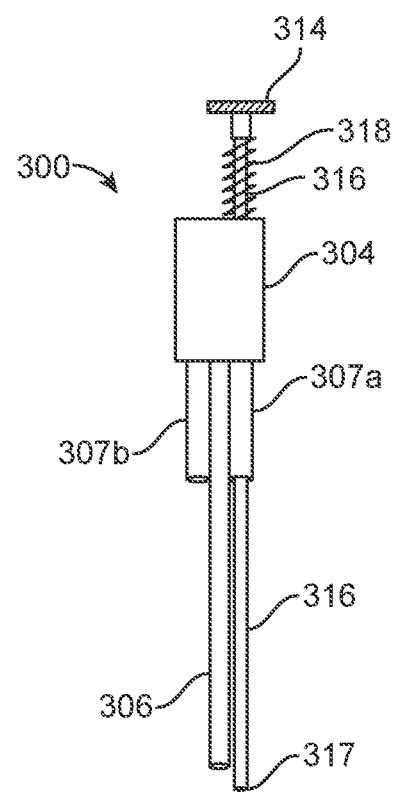
Figure 9C:
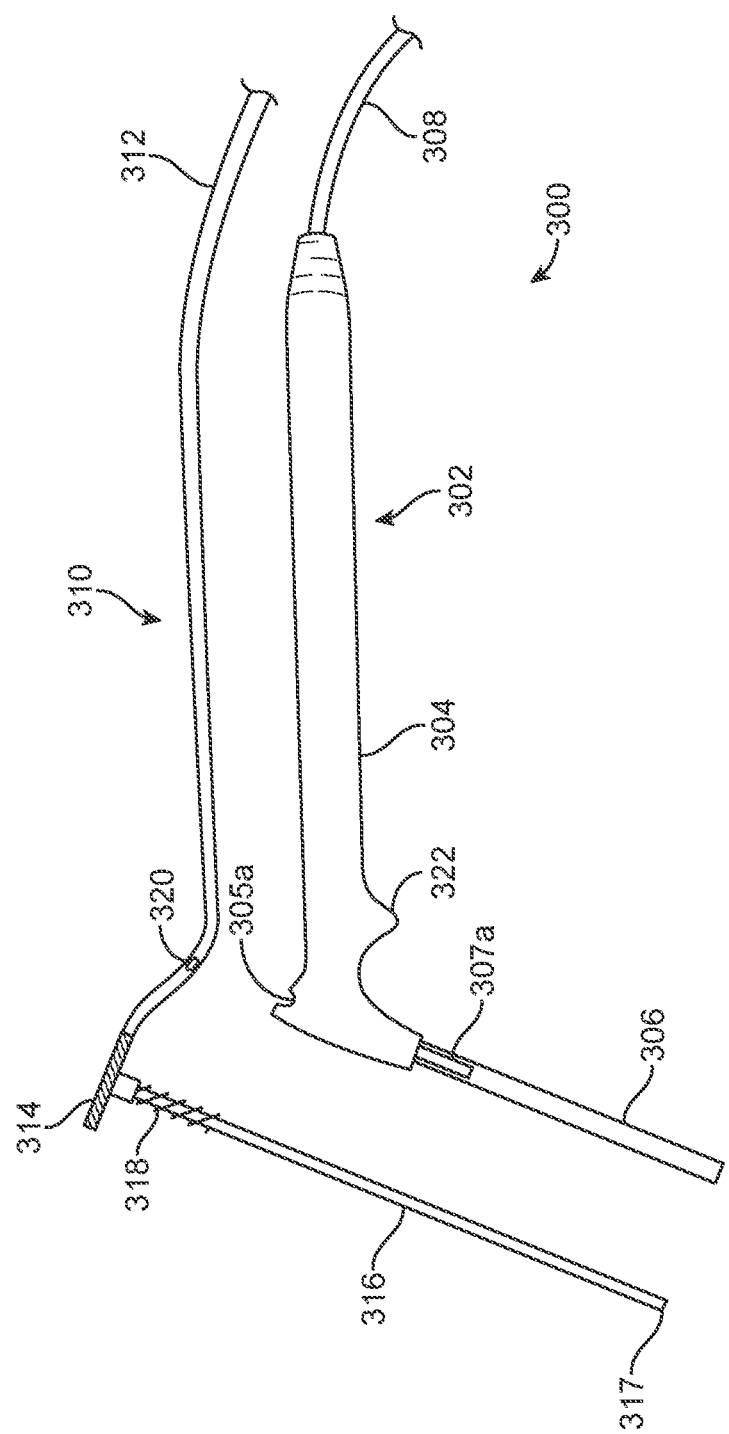

Referring now to FIGS. 9A-9C, one embodiment of an ear visualization system 300 is illustrated. The ear visualization system 300 includes an ear endoscope 302 and an optional suction device 310. The ear endoscope 302 includes a handle 304, a shaft 306 extending from one end of the handle 304, two tool couplers 307*a*, 307*b* (see FIG. 9B) on either side of the shaft 306, and a cable 308 extending from the opposite end of the handle 304. Imaging components pass through the handle 304, the shaft 306 and the cable 308, which components may be any of those described above and which are not shown in these figures. The handle 304 includes two suction shaft apertures 305*a*, 305*b* (not visible in these drawings, because they are on the top surface of the handle 304), through which the shaft 316 of the suction component 310 is advanced. The shaft 316 of the suction component 310 advances through one of the two tool couplers 307*a*, 307*b*, after exiting the distal end of the corresponding aperture 305*a*, 305*b*. The handle 304 may have any of a number of suitable sizes, shapes and weights, but in this embodiment it is configured to be held easily in a pencil grip by the physician. The handle 304 may be made of lightweight plastic, in some embodiments.

The suction component 310 includes a suction tube 312, a thumb depress portion 314, a suction control aperture 320, a suction shaft 316 with a distal end 317, and a spring 318 disposed over the suction shaft 316, between the thumb depress portion 314 and the handle 304. The suction shaft 316 extends through the suction shaft aperture 305*a* in the handle 304, through the tool coupler 307*a*, and alongside the visualization component shaft 306. As will be described further below, the user physician may depress the thumb depress portion 314 to advance the distal end 317 of the suction shaft 316 out of the distal end of the visualization shaft 306 and thus farther into the ear. When the user releases the thumb depress portion 314, the spring 318 automatically retracts the suction shaft 316 back along the visualization shaft 306, through the tool coupler 307*a* and the aperture 305*a*. The physician may use an index finger (or other finger) to cover the suction control aperture 320 to apply suction, and she may remove the finger from the hole to remove or reduce suction at the distal end 317 of the suction shaft 316.

FIG. 9B is a front view of the ear visualization system 300, which illustrates that this embodiment includes two suction tool couplers 307*a*, 307*b*, one on either side of the visualization component shaft 306. This embodiment thus also includes two suction shaft apertures 305*a*, 305*b*, each feeding into one of the two suction tool couplers 307*a*, 307*b*. The two tool couplers 307*a*, 307*b* facilitate holding and manipulation of the device 300 by either a right hand or a left hand, and placement of the suction tube/other tool either below or above the camera sensor. The visualization component shaft 306, the tool couplers 307*a*, 307*b* and the suction shaft 316, in some embodiments, may be made of metal, such as stainless steel or other biocompatible metal.

In some embodiments, the visualization component shaft 306 has an outer diameter of about 2.5 millimeters or less. Similarly, each of the tool couplers 307a, 307b may have an outer diameter of about 2.5 millimeters or less. The suction shaft 316 has an outer diameter sized to fit through the inner diameter of the tool couplers 307a, 307b. In some embodiments, the suction shaft 316 may have an outer diameter of about 1.1 millimeters or less.

FIG. 9C is a side view of the ear visualization system 300, with ear endoscope 302 separated from the suction device 310. In this embodiment, the ergonomic design of the handle 304 may be important for facilitating handling of the system 300 by the physician. For example, the handle 304 includes a finger grip feature 322, which may allow for easy gripping of the handle 304 with a middle finger (or other finger). The user's index finger may be used to control the suction control aperture 320, and the user's thumb may be used to control the thumb depress portion 314 of the suction component 310. In other embodiments, one of which is described below, the finger grip feature 322 may include a loop, an elastic ring or any other suitable shape.

In various alternative embodiments, one or more variations may be made to the ear endoscope device 300. For example, in some embodiments, the couplers 307a, 307b may extend the entire length (or along a longer portion but not the entire length) of the endoscope main shaft 306. In some embodiments, there may be only one coupler and one aperture, rather than two couplers 307a, 307b and two apertures 305a, 305b.

Figure 15:
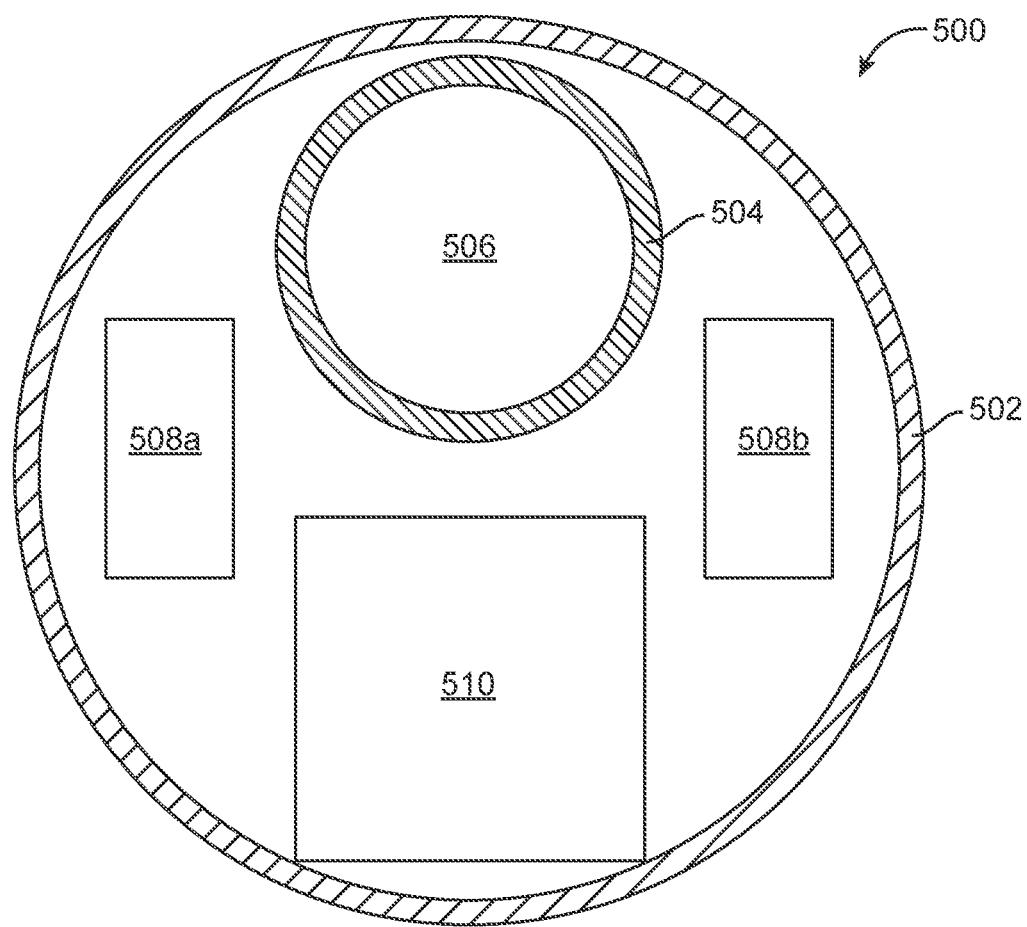
FIG. 15 is a distal-end view of a shaft of an ear endoscope, according to an alternative embodiment.

Referring to FIG. 15, in yet another alternative embodiment, an ear endoscope shaft 500 may include an outer shaft body 502, a tool guide 504 forming a tool lumen 506, two light sources 508a, 508b and an imaging sensor. The tool guide 504 and tool lumen 506, in this embodiment, are located inside the outer shaft body 502, unlike the previously described embodiments that place the suction tube through a coupler on the outside of the main endoscope shaft. In some embodiments, the tool guide 504 may be used for applying suction or advancing a suction device through the shaft 500. Alternatively, the tool guide 504 may be used for advancing any other suitable tool through the ear endoscope shaft 500, such as any tool listed in this application. This embodiment of FIG. 15 may be applied to any of endoscope embodiments described above or below to generate alternative embodiments.

Figure 10A:
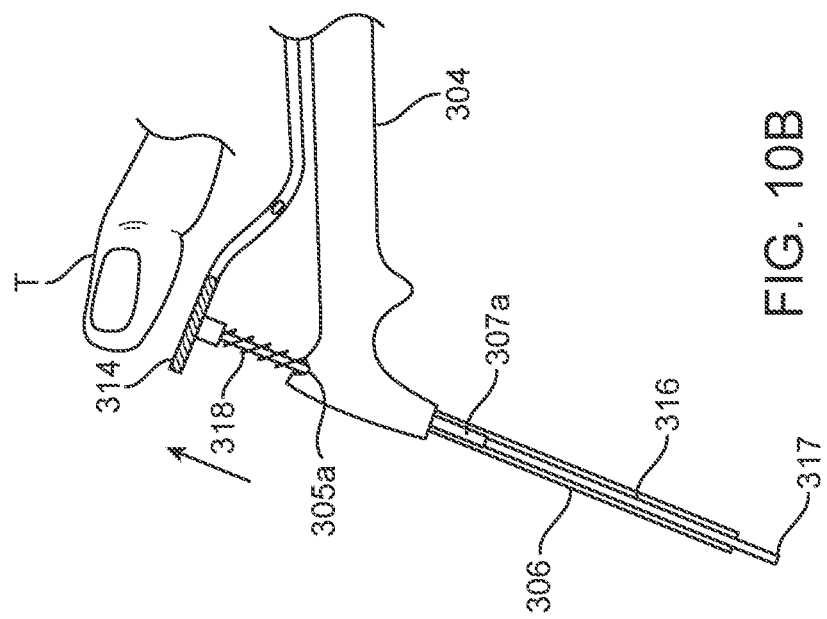
FIGS. 10A and 10B are side views of a portion of the combination device of FIGS. 9A-9C, illustrating a method for advancing and retracting a suction shaft relative to a visualization shaft, according to one embodiment.
Figure 10B:
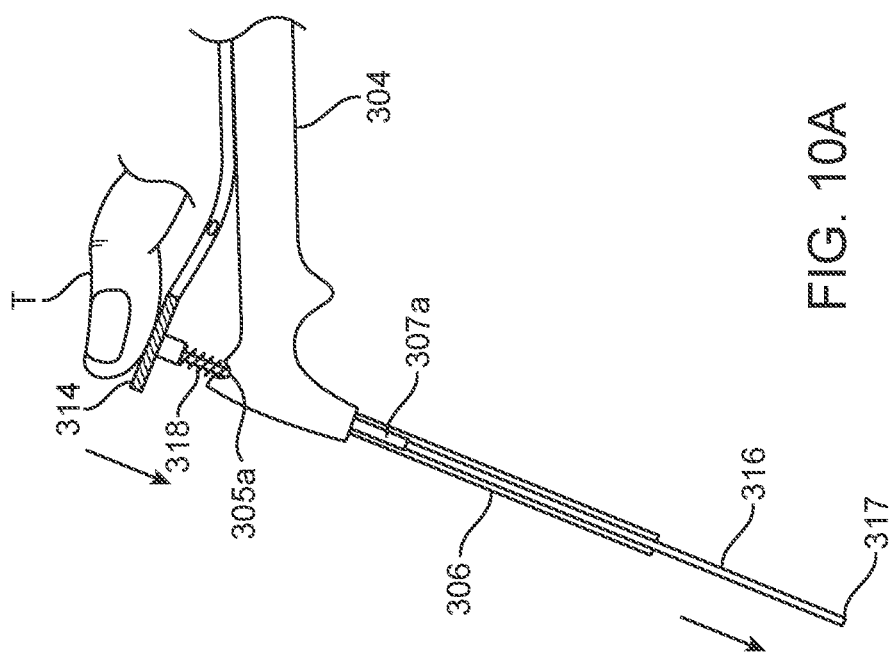

FIGS. 10A and 10B illustrate a method for advancing and retracting the suction shaft 316 in the ear visualization system 300, according to one embodiment. In FIG. 10A, the physician is depressing the thumb depress portion 314 of the suction component 310 with her thumb T. This advances the suction shaft 316 through the handle 304 and the tool coupler 307a, thus advancing the suction shaft 316 along the side of the visualization shaft 306. Thus, the distal end 317 of the suction shaft 316 would be advanced farther down into the patient's ear. In this configuration, the spring 318 is compressed. In FIG. 10B, the physician has released her thumb T from the thumb depress portion 314, allowing the spring 318 to expand and causing the suction shaft 316 to retract proximally through the tool coupler 307a and the handle 304. Thus, the physician can easily adjust the position of the distal end 317 of the suction shaft 316 relative to the visualization shaft 306.

In various embodiments, the distal end 317 of the suction shaft 316 may be positioned in a number of different locations relative to the distal end of the visualization shaft 306. When the suction shaft 316 is fully advanced, its distal end 317 may be located at, proximal to or distal to the distal end of the visualization shaft 306. Similarly, when the suction shaft 316 is fully retracted, its distal end 317 may be located at, proximal to or distal to the distal end of the visualization shaft 306. For example, in one embodiment, the distal end 317 of the suction shaft 316 may be disposed even with the distal end of the visualization shaft 306 in the fully retracted position and then may be advanced to a position distally beyond the distal end of the visualization shaft 306. In another embodiment, the distal end 317 of the suction shaft 316 may be disposed more proximally than the distal end of the visualization shaft 306 in the fully retracted position and then may be advanced to a position even with the distal end of the visualization shaft 306. Any combination of locations is possible, according to various alternative embodiments.

Figure 11:
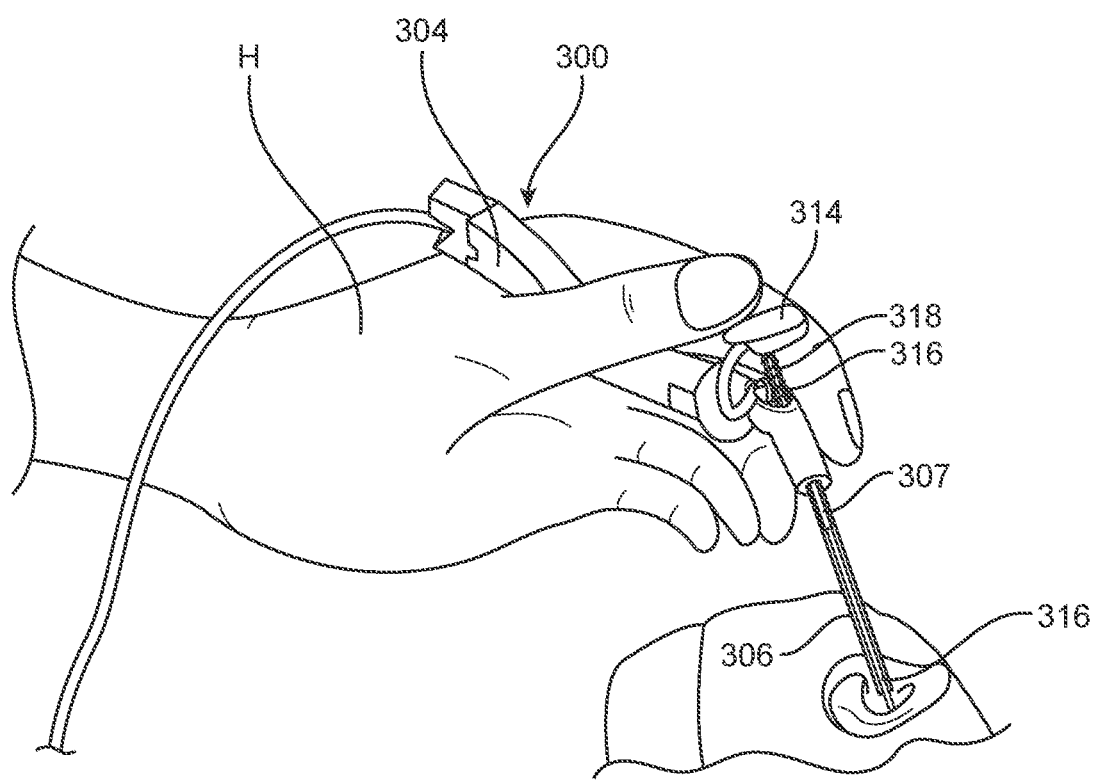
FIG. 11 is a perspective view of portion of a patient's head, including the ear, and a physician's hand holding the combination device of FIGS. 9A-10B.

Referring to FIG. 11, a physician's hand H is shown holding the combination device 300 over an anatomical model. As shown, the handle 304 fits comfortably in the hand H, with the middle finger on the bottom and the index finger on the top. The thumb is positioned on the thumb depress portion 314, and the visualization component shaft 306 and the suction shaft 316 are extended into the model. During an ear procedure, the physician might rest his or her hand on the patient's head, for support and stability and to prevent arm fatigue. The very light weight of the handle 304 and the device 300 in general make it easy to manipulate and hold.

Figure 12:
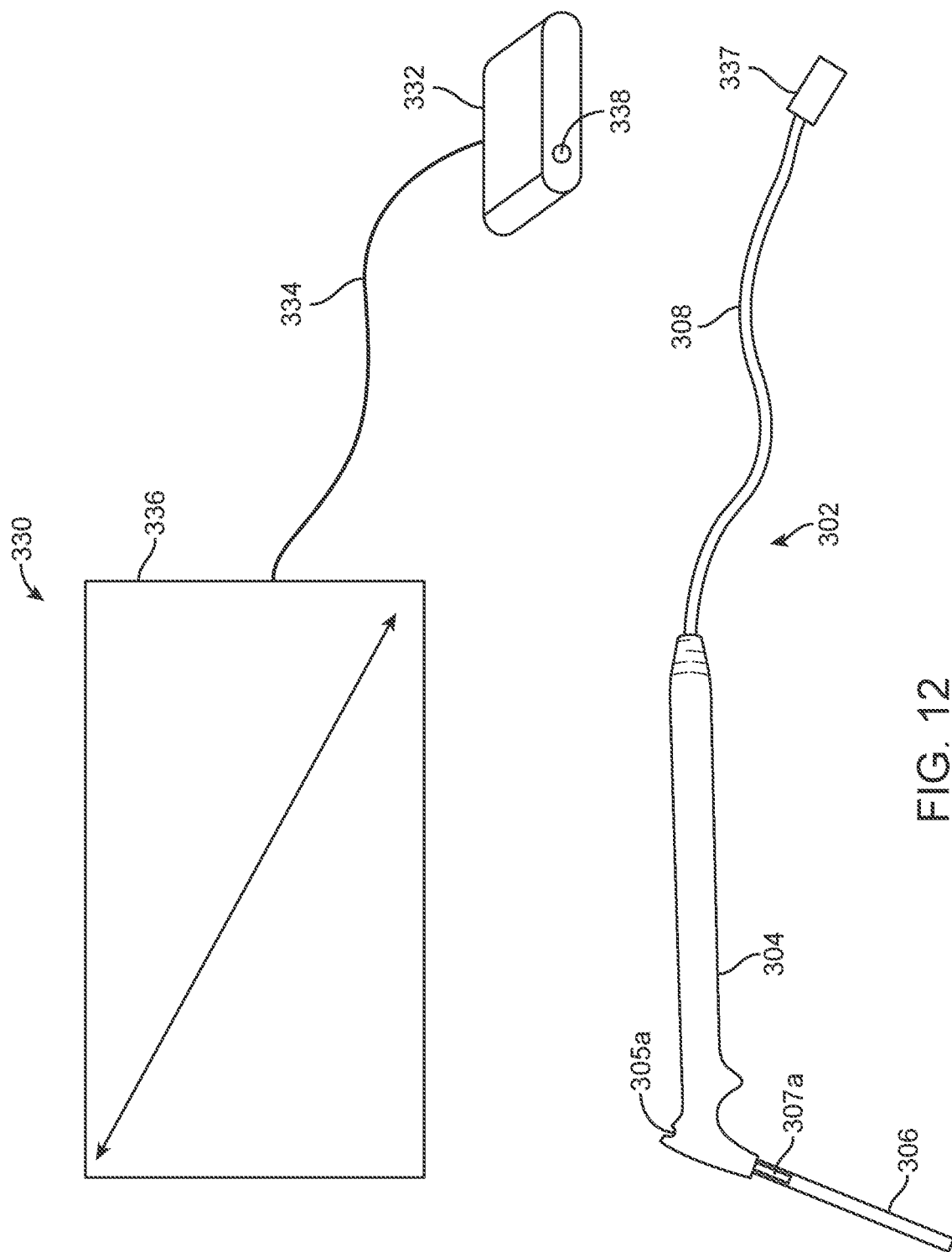
FIG. 12 is a perspective view of a visualization component of the combination device of FIGS. 9A-11, along with a viewing system, according to one embodiment.

Referring now to FIG. 12, in some embodiments, the ear visualization system 300 may include the ear endoscope 302 and a viewing system 330. The viewing system may include a video monitor 336, a console 332 and a cable 334 connecting the two. The console 332 may include a connector 338, into which a connector 337 on the visualization component 302 inserts. The various parts of the viewing system 330 may be any suitable off-the-shelf or custom components, according to various embodiments. In an alternative embodiment, the console 332 may include a built-in screen, rather than having a separate video monitor 336, and the endoscope 300 would connect to the console 332. In various embodiments, the ear endoscope 302 may be provided with the viewing system 330, with the suction device 310 or as a stand-alone device.

Figure 13A:
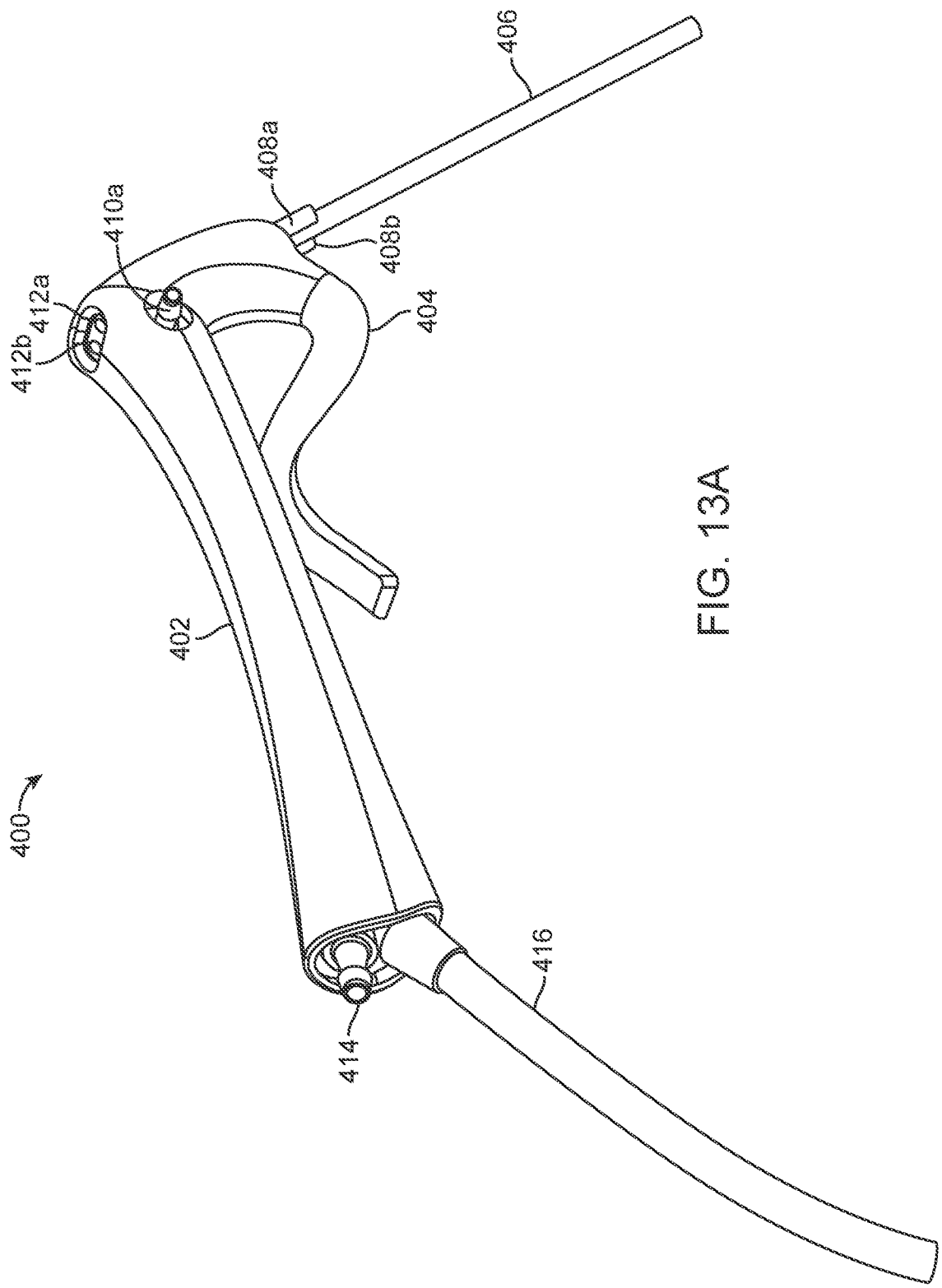
Figure 13B:
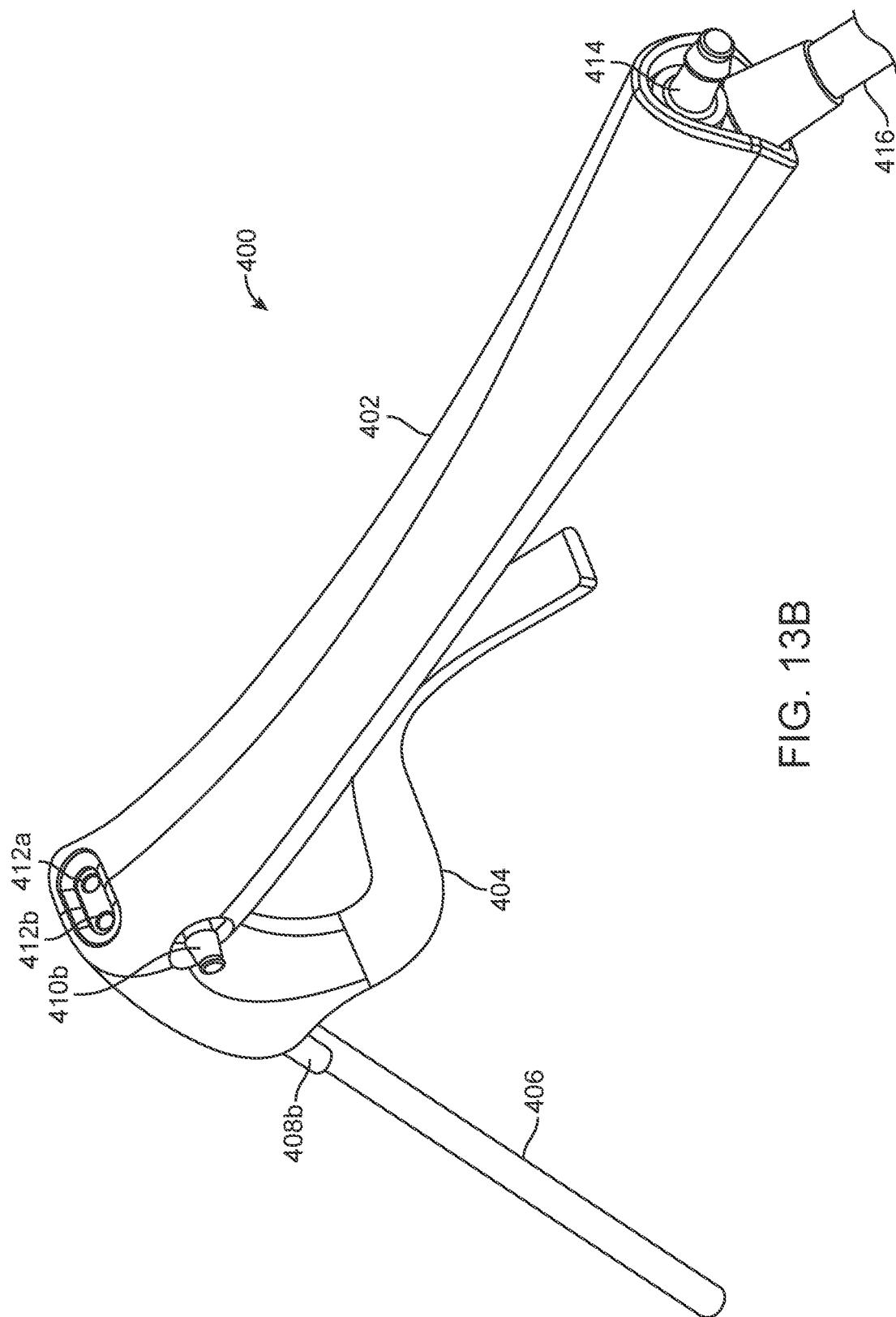

Referring now to FIGS. 13A-13C, another embodiment of an ear endoscope 400 is illustrated. In this embodiment the ear endoscope 400 includes a handle 402 with a finger loop 404, a shaft 406, two tool coupling shafts 408a, 408b, two side suction tube connection ports 410a, 410b, two suction tube insertion ports 412a, 412b, a rear suction tube connection port 414 and a sensor interface cable 416. In this embodiment, the ear endoscope 400 may be provided as a separate unit and may be used with an add-on suction device, or it may be provided with the suction device. In either case, a suction supply may be connected to the rear suction tube connection port 414, which is in fluid communication with a suction lumen running through the handle 402 and exiting at the two side suction tube connection ports 410a, 410b. One of the two side suction tube connection ports 410a, 410b may in turn be connected to a short suction tube, which is connected to a suction shaft that passes through one of the suction tube insertion ports 412a, 412b and one of the tool coupling shafts 408a, 408b, as will be described further below. Whichever of the two suction tube connection ports 410a, 410b is left open may be used by the physician as a suction control, by placing a finger over the open port 410a or 410b to apply suction or releasing the finger from the open port 410a or 410b to turn off suction.

The finger loop 404 on the handle 402 may be flexible in some embodiments and rigid in others. In alternative embodiments, the finger loop 404 may have any other suitable shape or size for facilitating gripping the endoscope 400. The finger loop 404 allows the physician user to hold and operate the ear endoscope 400 with one hand. In fact, the finger loop 404 may allow the physician to hold the handle 402 with one finger (middle finger, for example) and operate other functions of the device 400 with other fingers. For example, the user may pass a middle finger through the finger loop 404, use the thumb of the same hand to advance the suction tube, and use the index finger of the same hand to control suction by covering and uncovering the open port 410a or 410b. Alternatively, the fingers may be placed and used in a different configuration on the handle 402. As is evident from FIGS. 13A-13C, the shaft 406 is straight in this embodiment, but it is angled relative to the handle 402, so that the overall endoscope device 400 is angled, to allow the physician to place the shaft 406 in the ear canal without obstructing a direct viewing path into the ear canal.

Figure 14A:
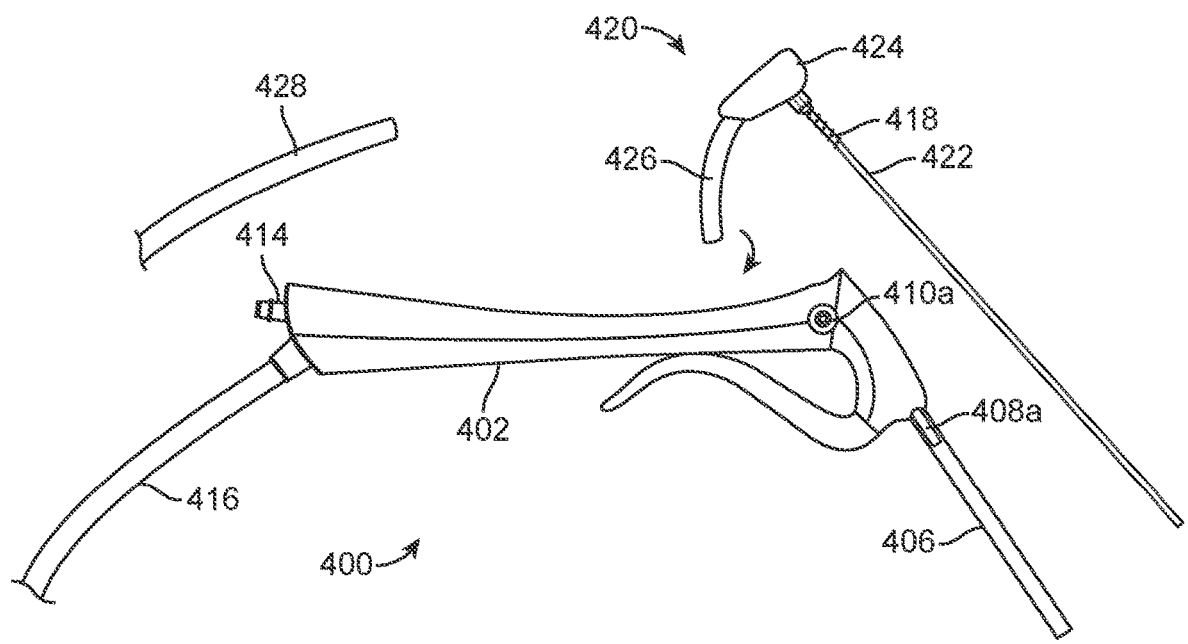
FIG. 14A is a side view of the ear endoscope device of FIGS. 13A-13C, with a detached optional suction device for the ear endoscope, according to one embodiment.
Figure 14B:
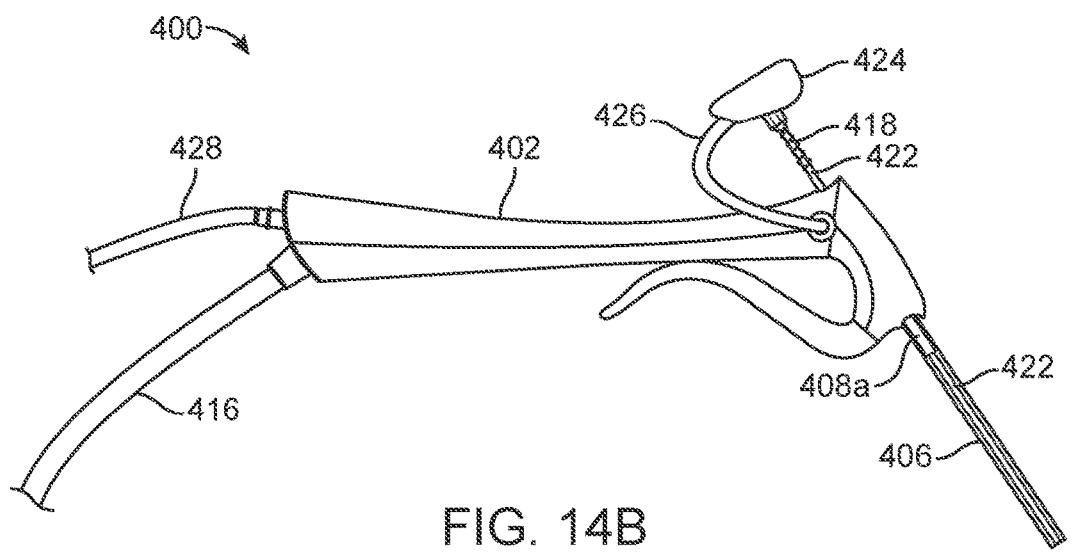
FIG. 14B is a side view of the ear endoscope and suction device of FIG. 14A, with the suction device attached to the ear endoscope.
Figure 14C:
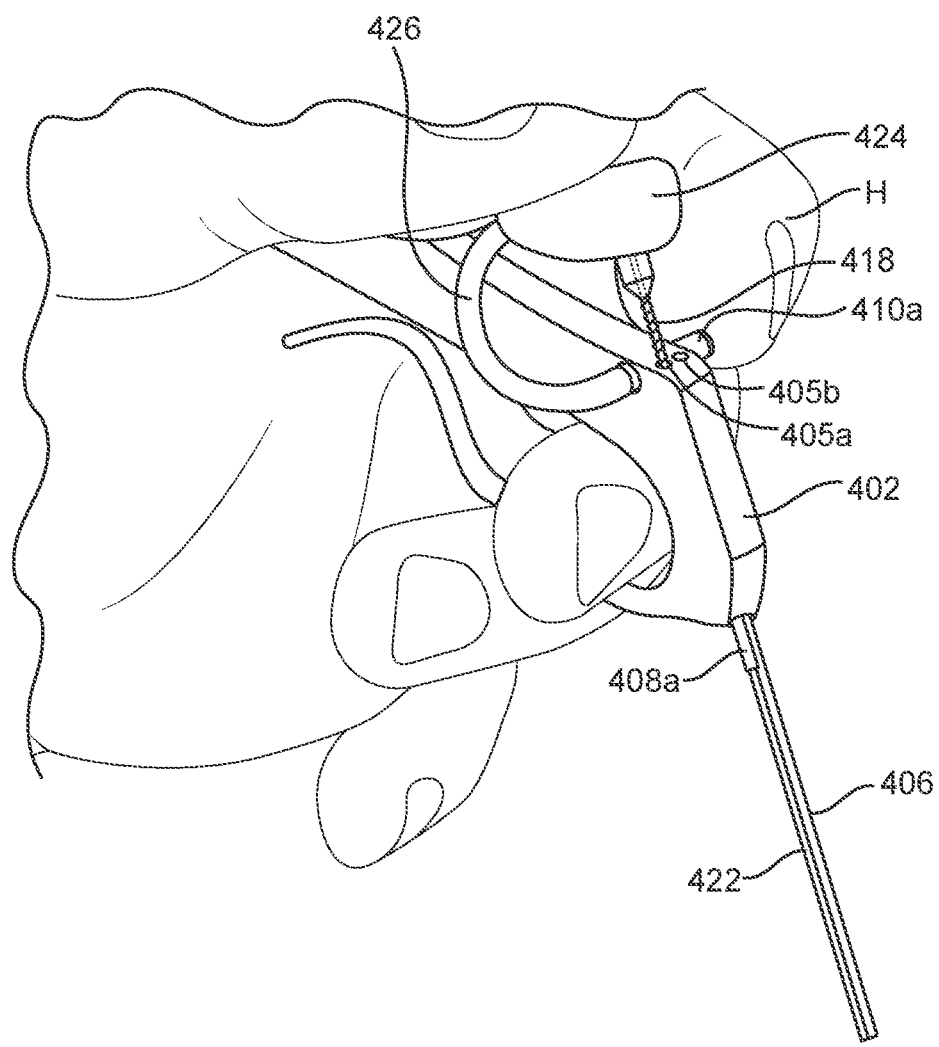
FIG. 14C is a perspective view of the ear endoscope with suction device of FIGS. 14A and 14B, shown in the left hand of a physician user.

Referring now to FIGS. 14A-14C, the ear endoscope 400 of FIGS. 13A-13C is now shown with an optional suction device 420. FIG. 14A shows the suction device 420 detached from the ear endoscope 400. The suction device 420 includes a suction shaft 422, connected to a thumb depress member 424, which is connected to a side suction tube 426. A spring is disposed over a proximal portion of the suction shaft 422, to provide for automatic retraction of the suction shaft 422 relative to the main shaft 406 of the ear endoscope 400, when the user releases pressure off of the thumb depress member 424. The suction device 420 may also include a rear suction tube 428. The suction shaft 422 is passed through either of the two suction tube insertion ports 412a, 412b and thus through the corresponding tool coupling shaft 408a, 408b. Side suction tube 426 may be connected to either of the two side suction tube connection ports 410a, 410b, leaving the opposite side port 410a, 410b open for finger control of suction. Additionally, the rear suction tube 428 is attached to the rear suction tube connection port 414, to supply suction force from a suction supply (such as wall suction, canister suction, etc.—not shown in FIG. 14A) to the suction device 420. As explained above, a suction lumen in the handle 402 of the endoscope 400 (not visible in the figures) connects the rear suction tube connection port 414 with the two side suction tube connection ports 410a, 410b.

FIG. 14B shows all the components of the suction device 420 attached to the ear endoscope. As shown in this figure, the spring 418 resides over the suction shaft 422 and between a bottom surface of the thumb depress member 424 and a top surface of the handle 402. When the user presses down on the thumb depress member 424, the suction shaft 422 advances distally along the main shaft 406, and the spring 418 compresses. When the user then releases pressure off of the thumb depress member 424, the suction shaft 422 automatically retracts proximally, relative to the handle 402 and the main shaft 406.

FIG. 14C shows a physician's left hand H holding the combined ear endoscope 400 and suction device. As illustrated here, the physician's thumb is positioned on the thumb depress member 424 and is used to advance the suction shaft 422. The physician's middle or ring finger may be placed through the finger loop 404 of the handle 402, and the physician's index finger may be placed over or removed from the open side suction tube connection port 410b, to control the application of suction through the suction shaft 422. If the physician prefers to hold the ear endoscope 400 in his right hand, the side suction tube 426 and suction shaft 422 may simply be shifted to the opposite side of the ear endoscope 400.

FIG. 15 is a cross-sectional view of a distal/shaft portion of an ear visualization device 500, according to one embodiment. The portion of the device 500 illustrated in FIG. 15 may be used with any of the embodiments described above or below. The illustrated portion of the device 500 includes an outer shaft 502, inside of which there is a suction shaft 504 forming a suction lumen 506. Also located inside the outer shaft 502 are a camera 510 and two sets of light fibers 508a, 508b, which are illustrated as rectangular but may be bundled in circular, ovoid or any other suitable shapes. In some embodiments, the inside of the outer shaft 502 may be solid or filled with a material, and the camera 510 and light fibers 508a, 508b may reside in lumens formed within the material in the outer shaft 502. The camera 510 may be located at or near the distal end of the outer shaft 502 and may be any kind of suitable camera, such as but not limited to a complementary metal-oxide-semiconductor (CMOS) or charge-coupled device (CCD) camera. The light source may be any type of suitable light source, as well, including but not limited to light fibers 508a, 508b, one or more light emitting diodes (LEDs), etc. Again, this is only one exemplary embodiment of the shaft portion of a device 500.

Figure 16B:
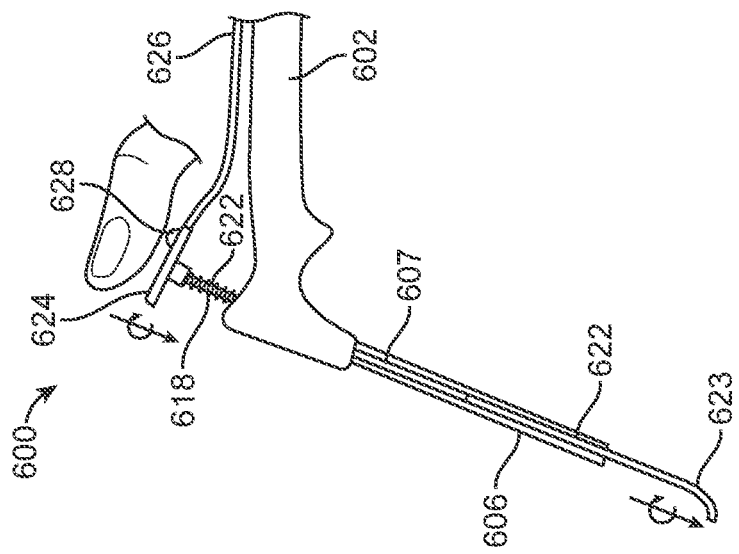
FIGS. 16A and 16B are side views of an ear endoscope with a curved tip suction shaft, showing the suction shaft advanced distally (FIG. 16A) and retracted proximally (FIG. 16B), according to one embodiment.
Figure 16A:
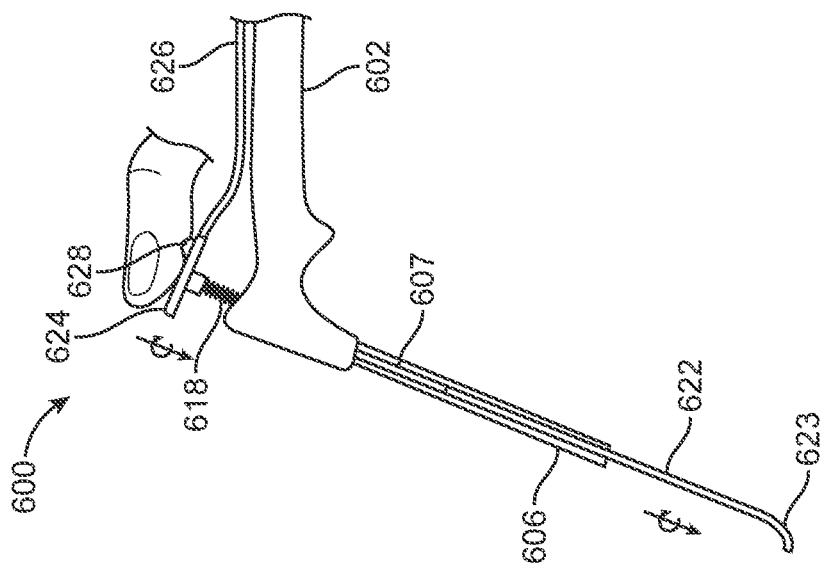

FIGS. 16A and 16B illustrate another embodiment of an ear visualization/suction device 600. As with previous embodiments, device 600 includes a handle 602, a main shaft 606 (or "endoscope shaft," which includes a camera at its distal end), a suction guide shaft 607 on the side of the main shaft 606, a thumb depress portion 624 attached to a suction shaft 622 and a suction tube 626, and a spring 618 disposed over a portion of the suction shaft 622 to automatically retract the suction shaft 622 when the user releases her thumb from the thumb depress portion 624 (as in FIG. 16B). In this embodiment, the suction shaft 622 of the ear visualization/suction device 600 further includes a curved distal tip 623, and the thumb depress portion 624 includes a surface feature 628. The physician user may apply pressure to the thumb depress portion 624 (as in FIG. 16A) and use the surface feature 628 (a bump in the present embodiment) to spin the thumb depress portion 624 and thus the suction shaft 622 and the curved distal end 623. In this way, the suction distal end 623 may be directed in multiple different directions to suction different areas within the ear. The curved distal tip 623 may have different shapes and angles and the surface feature 628 may also have many different shapes and configurations, some of which are described in further detail below. For example, in one alternative embodiment, the extreme end of the curved distal end 623 may be slanted, rather than the blunt/flat end illustrated in FIGS. 16A and 16B, which may help facilitated suctioning over surfaces as the distal end 623 is spun around.

Figure 17:
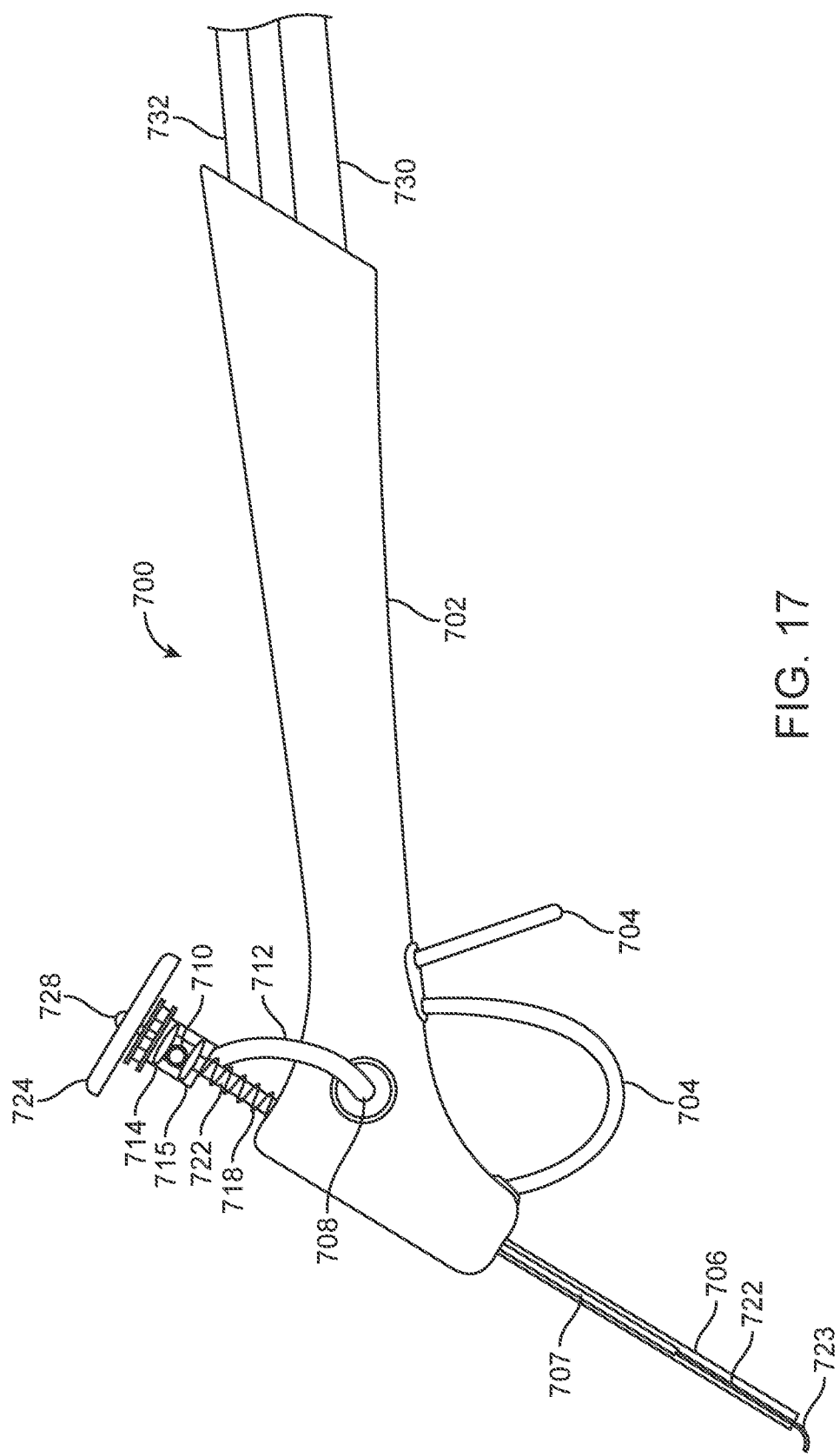
FIG. 17 is a side view of an ear endoscope with a curved tip suction shaft and a handle with a finger loop, according to an alternative embodiment.

FIG. 17 illustrates another embodiment of an ear visualization/suction device 700. This embodiment also includes a handle 702, which in this case is attached at its proximal end to an endoscope cable 730 and a suction tube 732, both of which pass through the body of the handle 702 to the front/distal end of the handle 702. Suction tube 732 passes through the body of the handle 702 and terminates at two suction ports 708 (only the left port is visible in FIG. 17), one on each side of the handle 702. One suction port 708 is attached to a short suction tube 712, which in turn attaches to a suction port 710 on a free spin suction member 715 that is disposed over, and spins freely around, the suction shaft 722. The suction port 710 on the free spin suction member 715 is in fluid communication with the lumen of the suction shaft 722, so that suction force passes through the port 710 and into the lumen of the shaft 722. In use, suction travels from the suction tube 732, through the handle 702, through the suction port 708, through the short suction tube 712, through the suction port 710, and down the suction shaft 722 to the distal end of the suction shaft 722. The physician user will cover an opposite-side, open suction port (corresponding to 708, but on the side of the handle 702 that is not visible in FIG. 17) with his finger to apply suction to the suction shaft 722 and will release his finger from the open suction port to allow suction to flow out of the open port and thus stop the flow of suction through the suction shaft 722.

As with the previously described embodiment, the ear visualization/suction device 700 includes a main shaft 706, which includes a camera at its distal end for visualizing the ear. It also includes a suction guide shaft 707, and a suction shaft 722 with a curved distal tip 723. The device 700 may also include a spring 718 disposed over the proximal portion of the suction shaft 722, between the top of the handle 702 and the bottom of the free spin suction member 715. The free spin suction member 715 is disposed over the proximal end portion of the suction shaft 722, just below the thumb depress member 724, which again includes a surface feature 728. The free spin suction member 715 houses two O-rings 714, one of which is positioned above the hole in the suction tube 722 into which the port 710 leads, and one of which is below the hole. The free spin suction member 715 and O-rings 714 form a liquid sealed chamber that will pass suction from the short suction tube 712, through the suction port 710 on the free spin suction member 715 and finally into the suction shaft 722. At the same time, the suction shaft 722 can be rotated, while the free spin suction member 715 stays in one place (does not rotate), thus preventing the short suction tube 712 from twisting around the suction shaft 722. Again, in this embodiment, when the user spins the thumb depress member 724, using the surface feature 728, the free spin suction member 715 does not rotate with the thumb depress member 724 or the suction shaft 722, but instead remains in the same place, by rotating freely over the suction shaft 722 as the shaft spins. In this way, the suction port 710 does not spin together with the suction shaft 722 but stays in one place. This is important, because if the free spin suction member 715, along with the suction port 710, were to spin around with the thumb depress member 724 and the suction shaft 722, the short suction tube 712 would twist around the suction shaft 722 and make it difficult for the user to spin the suction shaft 722. It would also prevent free, continuous, 360-degree rotation of the suction shaft 722 and could potentially also result in pulling off of one of the suction ports 708, 710, spinning the suction shaft 722 back to its original orientation, or even hampering advancement of the suction shaft 722 in and out of the ear. Advantageously, the free spin suction member 715 allows the user to spin the thumb depress member 724 and the suction shaft 722 continuously, 360 degrees or more, as much as desired, without twisting the short suction tube 712.

One additional feature of this embodiment of the ear visualization/suction device 700 is an adjustable finger loop 704 on the handle 702. In this embodiment, the user may place her finger (for example her middle or index finger) through the looped portion of the finger loop 704 and pull the free end of the finger loop 704 to tighten the looped portion. The looped portion may also be pulled, to make it larger. This is but one example of a finger hold member that may be included on the handle 702 to facilitate holding of the handle 702 using one finger. In one embodiment, the user may hold the device 700 with her middle finger, via the finger loop 704, and operate the device 700 with other fingers of the same hand (index finger and thumb, for example).

Figure 18A:
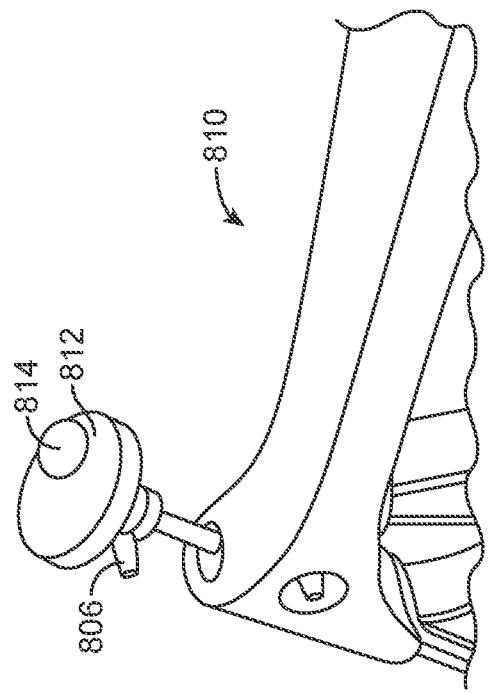
FIGS. 18A-18D are perspective views of four different embodiments of a thumb depress member of an ear endoscope with a curved tip suction shaft.

FIGS. 18A-18D are perspective views of a portion of an ear visualization/suction device, according to four different embodiments, where each embodiment includes a differently configured thumb depress member for rotating a suction shaft with a curved distal tip. Referring to FIG. 18A, one embodiment of an ear visualization/suction device 800 includes a generally circular thumb depress member 802 with an elliptical, off-center, raised surface feature 804. The thumb depress member 802 also includes a slightly concave upper surface for receiving the thumb. Having an off-center surface feature 804 allows the user to rest a finger (typically the thumb) against the surface feature 804 and ergonomically easy spinning of the suction shaft. Also pictured in this and the following embodiments are a handle 801, a handle suction port 808, a suction shaft 810, and a suction shaft suction port 806.

Figure 18B:
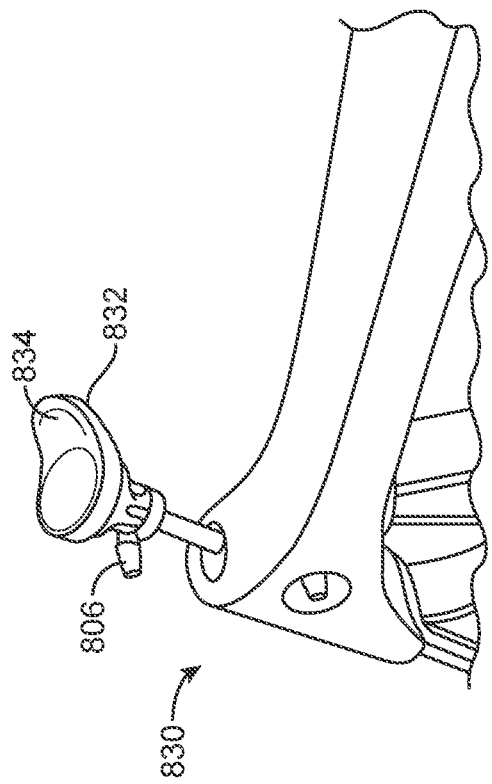
Figure 18C:
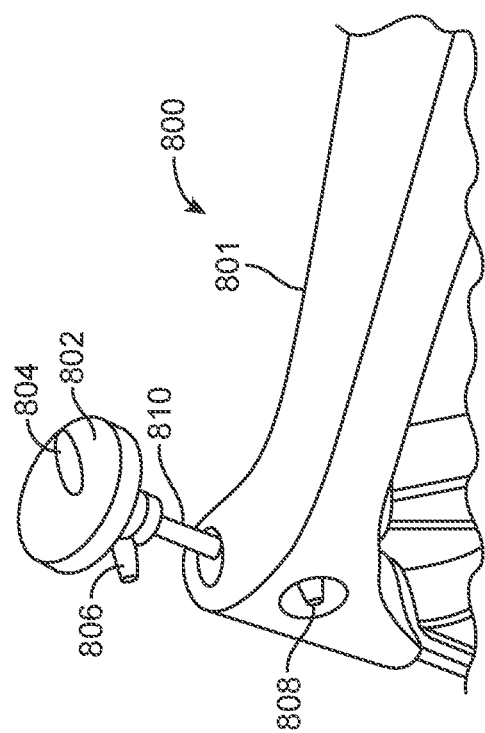
Figure 18D:
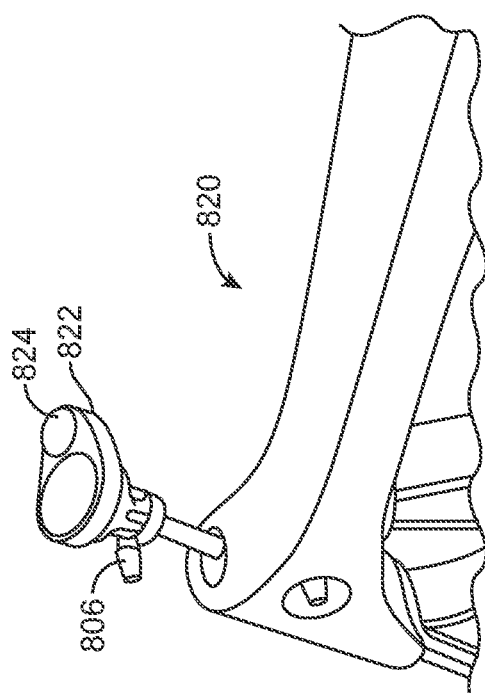

In the embodiment of FIG. 18B, the ear visualization/suction device 810 includes a similarly circular, slightly concave thumb depress member 812, with a more round shaped (or oval) surface feature 814. In the embodiment of FIG. 18C, the ear visualization/suction device 820 includes an asymmetrical, bean-shaped thumb depress member 822 with a round-shaped (or oval) raised surface feature 824 on a lateral portion of the thumb depress member 822. In the embodiment of FIG. 18D, the ear visualization/suction device 830 includes another asymmetrical thumb depress member 832 with a raised, upwardly curving edge at one side. As FIGS. 18A-18D illustrate, in any given embodiment, the thumb depress member and the surface feature may have any suitable shape, size and configuration.

Figure 19:
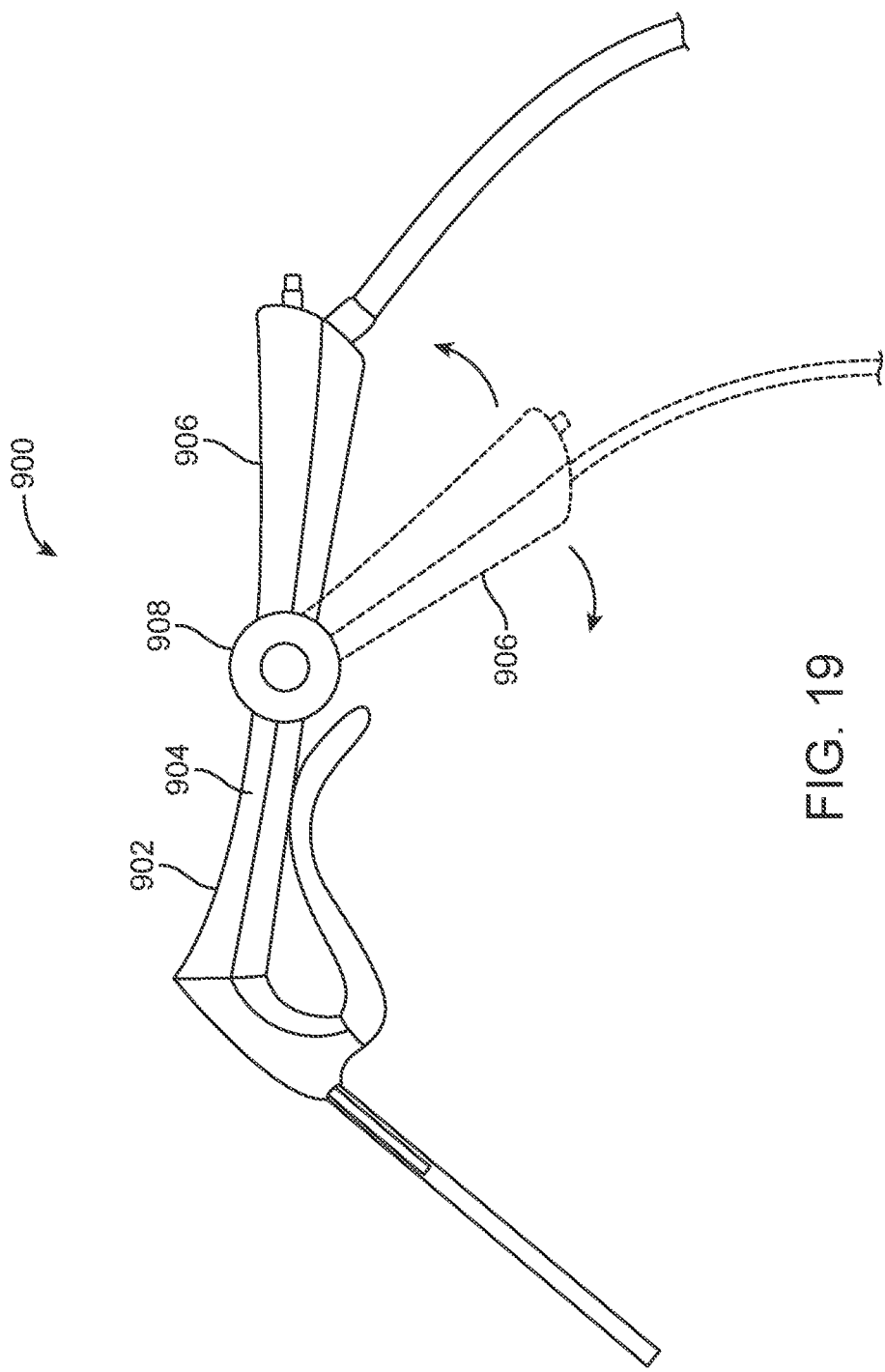
FIG. 19 is a side view of an ear endoscope device with an adjustable-angle handle, according to one embodiment.

Referring now to FIG. 19, another embodiment of an ear visualization/suction device 900 is illustrated. This embodiment includes many of the features of previous embodiments, which will not be explained again here. In addition, this embodiment of the device 900 includes an adjustable handle 902, which may make holding the handle 902 more comfortable for a given user. The handle 902 has a distal portion 904, a proximal portion 906, and an adjustment member 908 between the two. The adjustment member 908 acts as an axis, to allow the proximal portion 906 to rotate down (and back up as desired), so that the proximal portion 906 can be angled, relative to the distal portion 904. Thus, the user can direct the tip of device 900 in the direction of the ear canal (typically superiorly-posteriorly), regardless of whether the device 900 is being used in a left ear or a right ear, without changing the orientation of the user's entire hand. In various embodiments, the adjustment member 908 may have specific adjustment angles that the proximal portion 906 clicks into and/or may have a locking feature to allow the user to lock the proximal portion 906 in a desired angle. In alternative embodiments, the adjustment member 908 may be positioned farther distally or farther proximally along the body of the handle.

Figure 20:
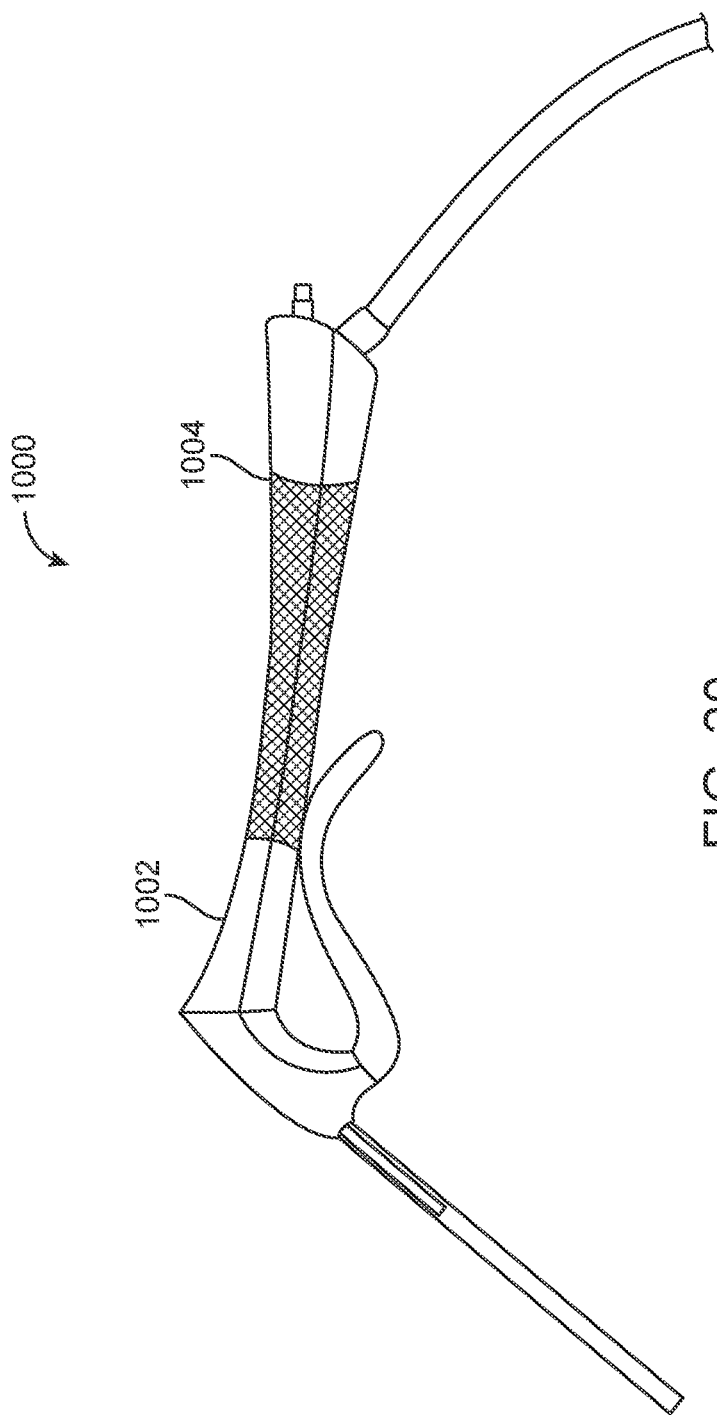
FIG. 20 is a side view of an ear endoscope device with a malleable handle, according to one embodiment.

Referring now to FIG. 20, in another embodiment, an ear visualization/suction device 1000 may include a handle 1002 that is malleable or includes a malleable section 1004. As with the similar embodiment, the malleable section 1004 allows the user to create an angle in the handle 1002, which may enhance ergonomics and comfort.

Figures 21A, 21B:
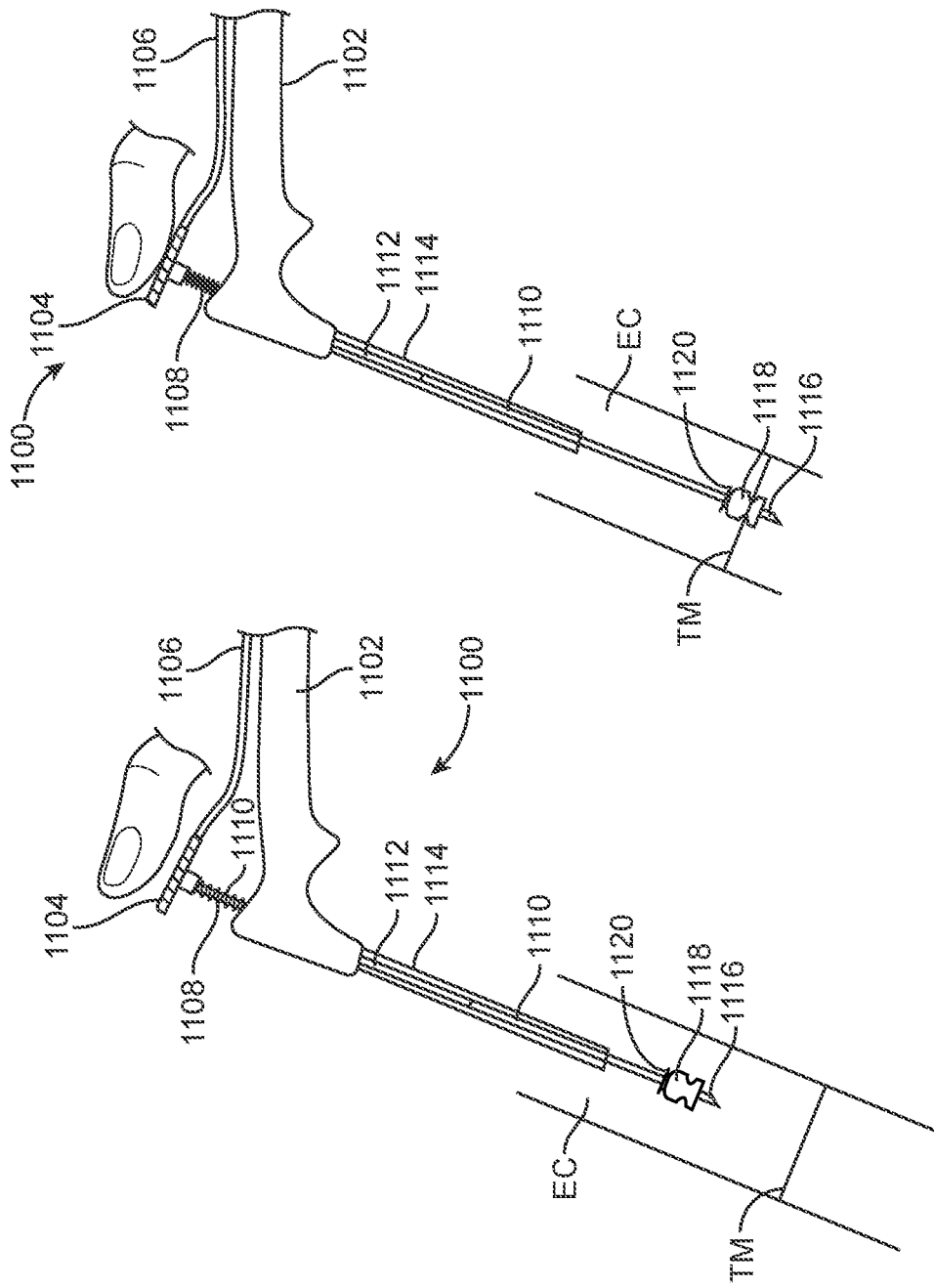
FIG. 21A is a side view of an ear tube placement, visualization and suction device, advanced partway into an ear canal, according to one embodiment.
FIG. 21B is a side view of the device of FIG. 21A, showing placement of an ear tube across the tympanic membrane, according to one embodiment.

Referring now to FIGS. 21A and 21B, one embodiment of an ear tube placement device 1100 is illustrated. In this embodiment, the ear tube placement device 1100 also functions as an ear visualization/suction device. Ear tubes are often placed in tympanic membranes TM (or "ear drums")

that lie between the outer ear (or "ear canal," labeled in the figures as EC) and the middle ear, primarily in children but also adults with frequent ear infections or other problems involving the middle ear. Although one handle/suction tube configuration is illustrated in FIGS. 21A and 21B, alternative embodiments may include any of the handle/suction configurations described in this disclosure. As with previously described embodiments, the device 1100 includes a handle 1102, a thumb depress portion 1104, a suction tube 1106, a main shaft 1114, a suction guide tube 1112, a suction shaft 1110, and a spring 1108 positioned over a proximal portion of the suction shaft 1110. This embodiment further includes a stop member 1120 located near the distal end of the suction shaft 1110 and a sharp distal tip 1116 on the suction shaft 1110. An ear tube 1118 may be part of the device 1100 or, more likely, the ear tube 1118 may be any currently available or to-be-developed ear tube, which is placed over the distal end 1116 of the suction shaft.

FIG. 21A illustrates the ear tube placement device 1100 in a pre-deployment position, with the ear tube 1118 mounted on the suction shaft 1110 and the distal end of the device 1100 being advanced into the ear canal EC. The thumb depress member 1104 is not yet depressed. FIG. 21B shows the device 1100 in position to deploy the ear tube 1118 in the tympanic membrane TM. In use, the suction shaft 1110 will typically be advanced toward the TM, until the sharp distal tip 1116 of the suction shaft 1110 pushes against the tympanic membrane TM to pierce the membrane. Next, the suction shaft 1110 will be further advanced, to push the ear tube 1118 through the new hole in the tympanic membrane TM, as illustrated in FIG. 21B. While 1118 is pushed through the hole, the stop member 1120 prevents 1118 from being pushed back by the TM and sliding back over suction shaft 1110, as the suction shaft 1110 advances through the TM. The stop member 1120 may be any suitable piece or surface feature on (or of) the suction shaft 1110, such as but not limited to a washer-like member, a raised ring on the suction shaft 1110, another tube disposed over the suction shaft 1110 or the like. In general, any piece or feature that will prevent the ear tube 1118 from sliding proximally during deployment will be suitable. After the ear tube 1118 is placed in the tympanic membrane TM, the suction shaft 1110 and/or the entire device 1100 may be retracted/pulled back, to slide the suction shaft 1110 out of the ear tube and the device 1100 out of the ear canal.

Figure 22:
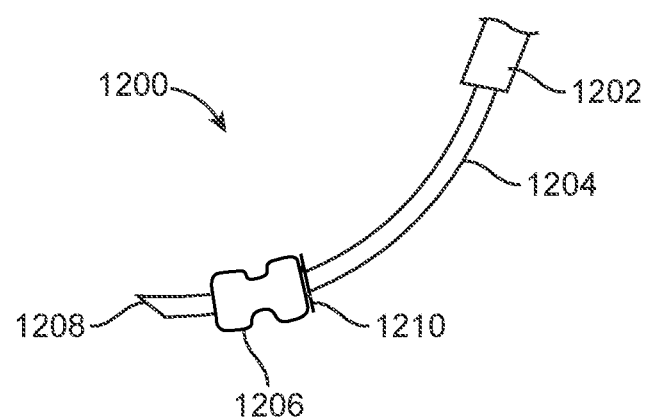
FIG. 22 is a side view of a curved distal end of an ear tube placement, visualization and suction device, according to one embodiment.

FIG. 22 illustrates a distal end of an alternative embodiment of an ear tube placement device 1200. In this embodiment, the main shaft 1202 includes a camera (not visible), as with previously described embodiments. The suction shaft 1204 is curved and ends in a sharp distal tip 1208. A stop member 1210 is disposed over the suction tube, and an ear tube 1206 is shown in position. In some embodiments, it may be advantageous to have a curved suction shaft 1204 with the ear tube placement device 1200, as this will allow it to reach different areas of the TM with slight spins of the suction shaft 1204.

Figure 23:
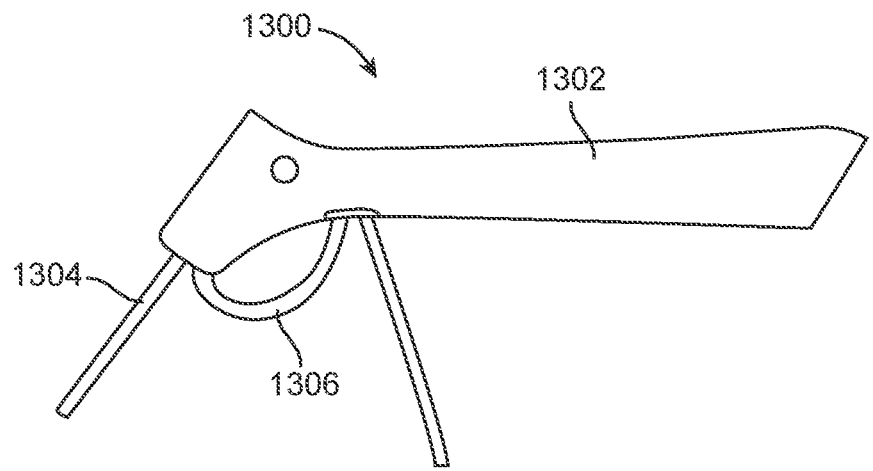
FIGS. 23 and 24 are side views of a portion of an ear visualization/suction device, illustrating a removable handle adjustment feature (FIG. 24)
Figure 24:
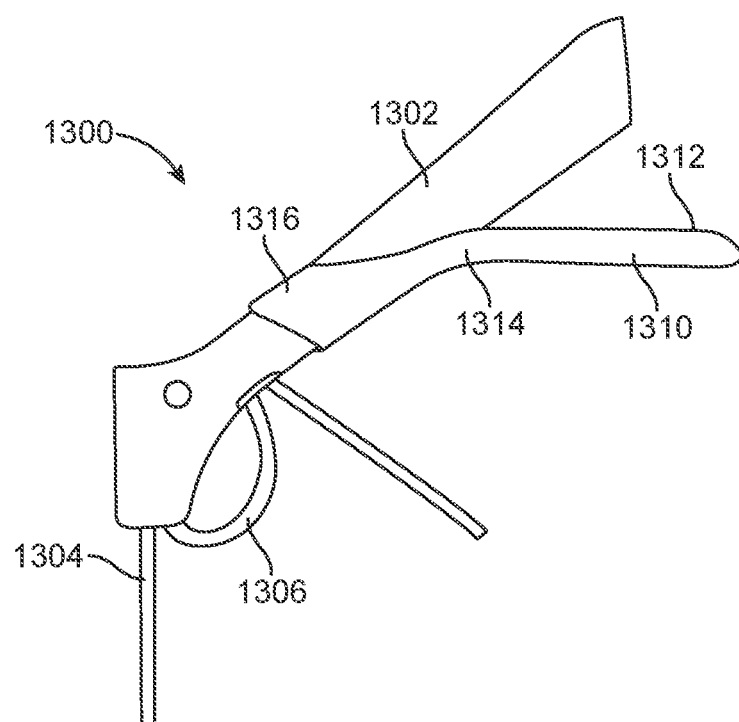

Referring now to FIGS. 23-26, in one embodiment of an ear visualization/suction device 1300, an optional handle angle adjustment member 1310 may be provided. FIG. 23 shows a portion of the device 1300 without the handle angle adjustment member 1310, illustrating a handle 1302, with a finger loop 1306, and a main shaft 1304. FIG. 24 shows the removable handle angle adjustment member 1310, which has a straight hand rest portion 1312, a curved portion 1314 and an attachment portion 1316 that attaches to the handle 1302. The attachment portion 1316 may be slid over the handle 1302 into place, such that the diameter of the handle 1302 and/or a stop member along the handle 1302 helps position the attachment portion 1316. In some embodiments, the attachment portion 1316 may be moved along the handle 1302 by the user, to any suitable location on the handle 1302. In various embodiments, the optional handle angle adjustment member 1310 may have any number of different sizes, shapes and angles. The curved portion 1314, for example, may have any suitable angle. In some embodiments, the curvature of the curved portion 1314 may be adjustable by the user—for example, it may be malleable. In some embodiments, the device 1300 may be provided with multiple, differently shaped handle angle adjustment members 1310, each having a different angle, shape and/or size.

Figure 25:
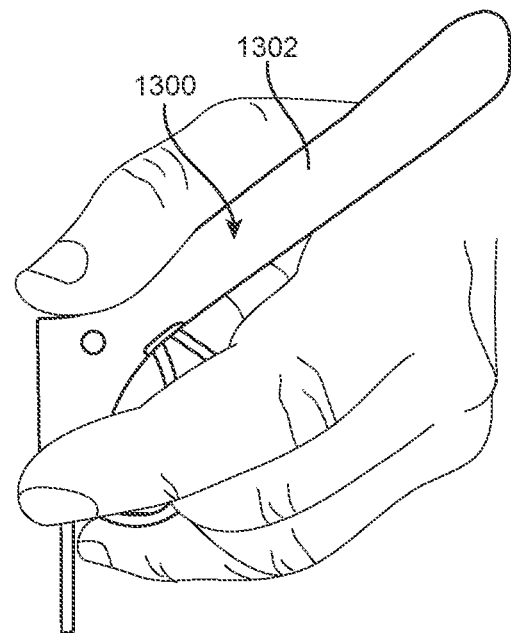
FIGS. 25 and 26 show the portion of the device from FIGS. 23 and 24 without (FIG. 25) and with (FIG. 26) an optional handle adjustment feature.
Figure 26:
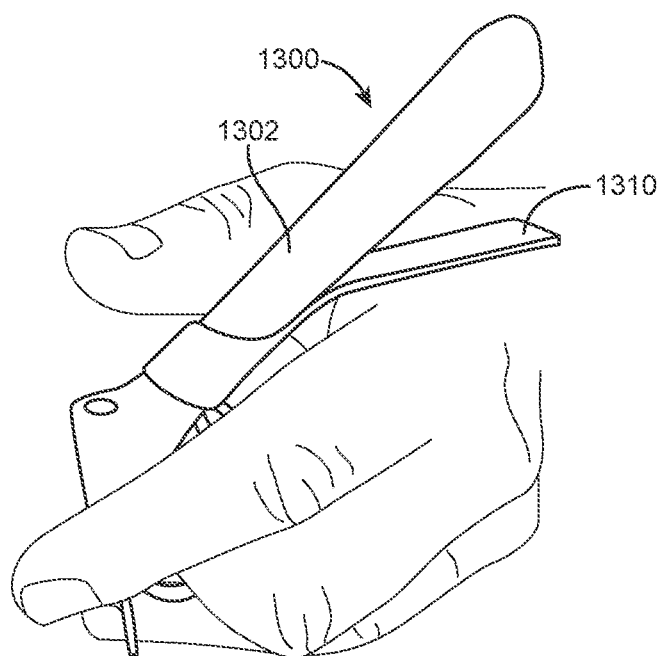

FIG. 25 shows a user holding the portion of the device 1300 without the handle angle adjustment member 1310. This figure illustrates a first relative angle between the user's hand and the handle 1302, as well as a first orientation of the main shaft 1304 of the device 1300, relative to the hand. FIG. 26 shows the same user's hand holding the device 1300 with the handle angle adjustment member 1310 attached. As seen here, the handle 1302 is now angled in a more upward direction, relative to the user's hand, and the main shaft 1304 of the device 1300 is angled toward the hand more than it was in FIG. 24. At the same time, however, the overall position of the user's hand is almost exactly the same in FIGS. 25 and 26. This illustrates that the handle angle adjustment member 1310 (or alternate embodiments thereof) may help a user access and visualize different parts of an ear without needing to assume awkward or uncomfortable hand positions.

FIGS. 27A and 27B are diagrammatic illustrations of one embodiment of a combined ear visualization/suction device 1400, shown in an orientation as if the device 1400 were being held in a left hand while inserted into a right ear (FIG. 27A) and a left ear (FIG. 27B). These two figures are simple representations of the device 1400, to illustrate how a working area in an ear canal might be limited in some scenarios. For example, FIG. 27B shows a representation of a left ear canal LEC and an area of interest in the left ear LE. The "area of interest" may refer to an area in the ear and/or one or more structures in the ear, such as but not limited to the tympanic membrane, an area just beyond the tympanic membrane in the middle ear, an area just before the tympanic membrane, or any other suitable area and/or structure in the ear. The device 1400 is being held in the left hand of the user (hand not shown), and the angle of view is represented in the figure by an eye symbol at the distal tip 1412 of the device 1400. The device 1400 includes a proximal bend 1410, which allows for a working area 1420 within the left ear canal LEC. The working area 1420 can be used for passing one or more tools for performing a procedure on the left ear LE area of interest. As FIG. 27B illustrates, when a user holds the device 1400 in his left hand and accesses the left ear canal LEC with the device 1400, the working area 1420 is sufficient for passing one or more tools, because it has a relatively large entry opening (the opening into the ear canal from outside the patient).

In contrast, referring to FIG. 27A, when the left handed user uses the device 1400 to access a right ear canal REC to view an area of interest in the right ear RE, this embodiment of the device 1400 may cut off the entry opening of a working area 1414, which may make it more difficult for the user to insert working tools into the ear canal REC. Although the overall size of the working area 1414 in FIG. 27A is approximately the same as the size of the working area 1420 in FIG. 27B, the configuration of the working area 1414 for a left handed user in a right ear canal REC may be problematic for passage of tools. This may require the user to position his/her hand in an awkward position or insert tools through the ear canal REC in an awkward way. The same problem may occur if a person holds the device 1400 in the right hand and uses the device 1400 in the left ear canal LEC.

FIGS. 28A and 28B are diagrammatic illustrations of an alternative embodiment of a combined ear visualization/suction device 1500, shown in an orientation as if the device 1500 were being held in a left hand while inserted into a right ear (FIG. 28A) and a left ear (FIG. 28B). In this embodiment, the device 1500 includes a proximal bend 1510 and a distal bend 1520, closer to the distal end 1522 of the device 1500. Thus, when held in the user's left hand and inserted into the right ear canal REC, the resulting working area 1524 has a sufficiently large opening and overall width to allow for tool passage. The distal bend 1520 may be formed in any of a number of ways and may be either fixed or adjustable in various embodiments. For example, in some embodiments, a distal portion of the device 1500 may be malleable, so the user can form and adjust the distal bend 1520. In other embodiments, the distal bend 1520 or a distal portion of the device 1500 may be rotatable. Alternatively, the view of the camera at the distal end 1522 of the device 1500 may be rotated or otherwise adjusted, for example by electronic adjustment, to allow for the desired viewing angle.

FIG. 28B shows the device 1500 with the distal bend 1520 adjusted to have a different angle, designed to access the left ear canal LEC and view the left ear area of interest LE. In this scenario, the working area 1530 is also sufficiently wide to allow for tool passage. Various alternative embodiments may have any number, location and angle of bends. In one embodiment, a left-handed device and a right-handed device may be provided.

The above description of embodiments and features of various devices and methods is believed to be complete. The embodiments are meant to exemplary in nature, however, and not exhaustive. Thus, their description should not be interpreted as limiting the scope of the invention.

We claim:

1. A method for facilitating a surgical procedure in a middle ear of a patient, the method comprising:
   holding a handle of an ear visualization and suction device with one hand;
   advancing a distal end of a rigid visualization shaft and a distal end of a rigid suction shaft of the ear visualization and suction device through an opening in a tympanic membrane and into the middle ear, wherein the rigid suction shaft passes through a first suction shaft guide tube located external, to the side of, and parallel with, the visualization shaft;
   viewing an anatomical structure in the middle ear with a camera in the rigid visualization shaft;
   applying suction in the middle ear via the distal end of the rigid suction shaft;
   advancing the rigid suction shaft through the first suction shaft guide tube to position the distal end of the rigid suction shaft beyond the distal end of the rigid visualization shaft;
   performing the surgical procedure in the middle ear, while continuing to view and apply suction in the middle ear with the visualization and suction device; and
   removing the ear visualization and suction device from the middle ear.

2. The method of claim 1, wherein the method further comprises, before advancing the ear visualization and suction device into the ear:
   advancing the proximal end of the suction shaft into a distal end of the first suction shaft guide tube and then through an opening in the handle;
   placing a spring over the proximal end of the suction shaft; and
   attaching the proximal end of the suction shaft to a thumb depress member, wherein advancing the rigid suction shaft through the first suction shaft guide tube comprises depressing the thumb depress member.

3. The method of claim 2, wherein the ear visualization and suction device further comprises a second suction shaft guide tube on an opposite side of the visualization shaft from the first suction shaft guide tube, and wherein the method further comprises selecting either the first suction shaft guide tube or the second suction shaft guide tube in which to place the suction shaft.

4. The method of claim 2, further comprising releasing the thumb depress member to allow the spring to automatically retract, thus retracting the suction shaft relative to the visualization shaft.

5. The method of claim 2, wherein the ear visualization and suction device further comprises a second suction shaft guide tube on an opposite side of the visualization shaft from the first suction shaft guide tube, the method further comprising:
   removing the thumb depress member from the proximal end of the suction shaft;
   removing the suction shaft from the first suction shaft guide tube;
   inserting the suction shaft into the second suction shaft guide tube; and
   reattaching the proximal end of the suction shaft to the thumb depress member.

6. The method of claim 5, further comprising:
   advancing the distal end of the visualization shaft and the distal end of the suction shaft through an opening in a tympanic membrane and into a middle ear of the patient's other ear;
   repeating at least some of the steps of the method of claim 2 in the middle ear of the patient's other ear.

7. The method of claim 2, wherein the distal end of the rigid suction shaft comprises a curved distal tip, and wherein the method further comprises spinning the thumb depress member with a thumb to spin the curved distal tip inside the patient and thus provide suction in a different direction.

8. The method of claim 1, further comprising:
   applying suction to the anatomical structure or a man-made structure in the middle ear to hold onto the anatomical structure or the man-made structure with the distal end of the suction shaft; and
   moving the anatomical structure or the man-made structure with the distal end of the suction shaft.

9. The method of claim 1, wherein viewing the anatomical structure comprises:
   illuminating the anatomical structure using an illumination member located at the distal end of the visualization shaft; and
   visualizing with a camera located at the distal end of the visualization shaft.

10. The method of claim 1, wherein the anatomical structure comprises one or more bones or other tissues of the middle ear.

11. The method of claim 1, further comprising resting the one hand holding the handle of the visualization and suction device on the patient to steady the visualization and suction device during at least part of the surgical procedure.

12. The method of claim 1, wherein applying the suction comprises using one finger of the one hand to cover a suction port on the handle, and wherein removing the one finger to uncover the suction port reduces or stops the application of suction.

13. The method of claim 1, wherein holding the handle comprises holding the handle with one finger of the one hand via a finger loop on the handle so that all other fingers of the one hand are free.

14. The method of claim 1, wherein the suction shaft has an outer diameter of no more than 1.1 millimeters and the visualization shaft has an outer diameter of no more than 2.5 millimeters.

\* \* \* \* \*